United States Patent
Saitoh

(10) Patent No.: US 9,125,628 B2
(45) Date of Patent: Sep. 8, 2015

(54) DEVICE FOR SENSING HUMAN BODY ABNORMALITY BY STANDING-WAVE RADAR AND METHOD FOR USING SAME

(71) Applicant: Mitsumasa Saitoh, Yokohama (JP)

(72) Inventor: Mitsumasa Saitoh, Yokohama (JP)

( * ) Notice: Subject to any disclaimer, the term of this patent is extended or adjusted under 35 U.S.C. 154(b) by 0 days.

(21) Appl. No.: 14/234,725

(22) PCT Filed: Sep. 21, 2012

(86) PCT No.: PCT/JP2012/074299
§ 371 (c)(1),
(2) Date: Jan. 24, 2014

(87) PCT Pub. No.: WO2013/042786
PCT Pub. Date: Mar. 28, 2013

(65) Prior Publication Data
US 2014/0155729 A1    Jun. 5, 2014

(30) Foreign Application Priority Data

Sep. 21, 2011  (JP) ................................. 2011-205460
Feb. 4, 2012  (JP) ................................. 2012-022579

(51) Int. Cl.
*G08B 23/00*    (2006.01)
*A61B 5/00*    (2006.01)
(Continued)

(52) U.S. Cl.
CPC ............. *A61B 5/7282* (2013.01); *A61B 5/0059* (2013.01); *A61B 5/0077* (2013.01); *A61B 5/01* (2013.01); *A61B 5/024* (2013.01);
(Continued)

(58) Field of Classification Search
CPC ................... A61B 2565/0204; A61B 5/02055
USPC ....................................................... 340/573.1
See application file for complete search history.

(56) References Cited

U.S. PATENT DOCUMENTS

2006/0064037 A1 *  3/2006  Shalon et al. ................. 600/586
2008/0319375 A1 * 12/2008  Hardy ............................. 604/22

FOREIGN PATENT DOCUMENTS

JP     9-28681 A    2/1997
JP     H10-239426 A   9/1998
(Continued)

OTHER PUBLICATIONS

International Search Report (ISR) (PCT Form PCT/ISA/210) dated Jan. 8, 2013, in PCT/JP2012/074299.
(Continued)

*Primary Examiner* — Shirley Lu
(74) *Attorney, Agent, or Firm* — McGinn IP Law Group, PLLC

(57) ABSTRACT

LEDs arranged in a circle, a standing-wave laser module, a board with a computation unit provided thereon, and an LED control unit are disposed inside a case. Illumination light is irradiated outward from the LEDs, and microwaves are transmitted from the standing-wave laser module and the reflected waves are detected. The computation unit combines the transmitted waves and the reflected waves to detect standing waves, and the distance to the body off which the waves are reflected and minute displacements (e.g., pulse and respiration) are detected on the basis of the standing waves. Thus, merely installing the present invention in lieu of existing illumination apparatuses installed in restrooms, bathing rooms, corridors, and the like allows the position of a human body, and the respiratory rate, heart rate, and the like thereof to be detected, and allows sudden changes to the condition of the detected human body to be rapidly detected.

18 Claims, 22 Drawing Sheets

(51) Int. Cl.

| | |
|---|---|
| G01S 13/40 | (2006.01) |
| G08B 21/04 | (2006.01) |
| A61B 5/024 | (2006.01) |
| A61B 5/08 | (2006.01) |
| A61B 5/11 | (2006.01) |
| A61B 5/113 | (2006.01) |
| F21K 99/00 | (2010.01) |
| F21V 23/04 | (2006.01) |
| H05B 33/08 | (2006.01) |
| H05B 37/02 | (2006.01) |
| A61B 5/01 | (2006.01) |
| A61B 5/18 | (2006.01) |
| A61B 19/00 | (2006.01) |
| G01S 13/88 | (2006.01) |
| F21V 33/00 | (2006.01) |
| F21V 3/00 | (2015.01) |
| F21V 23/00 | (2015.01) |
| F21Y 101/02 | (2006.01) |
| A61B 5/0205 | (2006.01) |
| A61B 5/097 | (2006.01) |

(52) U.S. Cl.
CPC ............ *A61B 5/0816* (2013.01); *A61B 5/1102* (2013.01); *A61B 5/113* (2013.01); *A61B 5/1128* (2013.01); *A61B 5/18* (2013.01); *A61B 5/4818* (2013.01); *A61B 5/7257* (2013.01); *A61B 19/5202* (2013.01); *F21K 9/1355* (2013.01); *F21V 23/0442* (2013.01); *F21V 33/0064* (2013.01); *G01S 13/40* (2013.01); *G01S 13/886* (2013.01); *G08B 21/04* (2013.01); *G08B 21/043* (2013.01); *H05B 33/0854* (2013.01); *H05B 37/0227* (2013.01); *A61B 5/02055* (2013.01); *A61B 5/097* (2013.01); *A61B 2562/0204* (2013.01); *F21K 9/135* (2013.01); *F21V 3/00* (2013.01); *F21V 23/006* (2013.01); *F21Y 2101/02* (2013.01); *Y02B 20/44* (2013.01)

(56) References Cited

FOREIGN PATENT DOCUMENTS

| | | |
|---|---|---|
| JP | 3057438 B2 | 6/2000 |
| JP | 2003-57028 A | 2/2003 |
| JP | 2003-132704 A | 5/2003 |
| JP | 2003-227873 A | 8/2003 |
| JP | 2005-326345 A | 11/2005 |
| JP | 2006-42201 A | 2/2006 |
| JP | 2006-255141 A | 9/2006 |
| JP | 2006-258467 A | 9/2006 |
| JP | 2006-285795 A | 10/2006 |
| JP | 2007-71605 A | 3/2007 |
| JP | 2007-78518 A | 3/2007 |
| JP | 2007-94942 A | 4/2007 |
| JP | 2009-55997 A | 3/2009 |
| JP | 2009-162709 A | 7/2009 |
| JP | 2009-250661 A | 10/2009 |
| JP | 2010-66877 | 3/2010 |
| JP | 2010-132444 A | 6/2010 |
| JP | 2011-34938 A | 2/2011 |
| JP | 2011-154993 A | 8/2011 |
| JP | 2011-165033 A | 8/2011 |
| WO | WO 2010/134367 A1 | 11/2010 |

OTHER PUBLICATIONS

Japanese Office Action dated Mar. 6, 2012, with partial English translation.

Japanese Office Action dated Jul 17, 2012, with partial English translation.

\* cited by examiner

A: AMPLITUDE OF THE SIGNAL SOURCE
c: SPEED OF LIGHT f: FREQUENCY $\begin{cases} f(t) = f_o + f_d \\ f_d = \dfrac{f_w}{t_w} t \end{cases}$ FREQUENCY VARIES IN A STEPWISE FASHION FROM
$f = f_o - f_w/2$ TO $f = f_o + f_w/2$ $$\triangle \Phi = \frac{4\pi(fd + fd1)}{c} dk$$

$$dk = \frac{c}{4\pi(fd - fd1)} \triangle \Phi$$

PHASE SEQUENCE = ea→eb→ec

FIG. 18
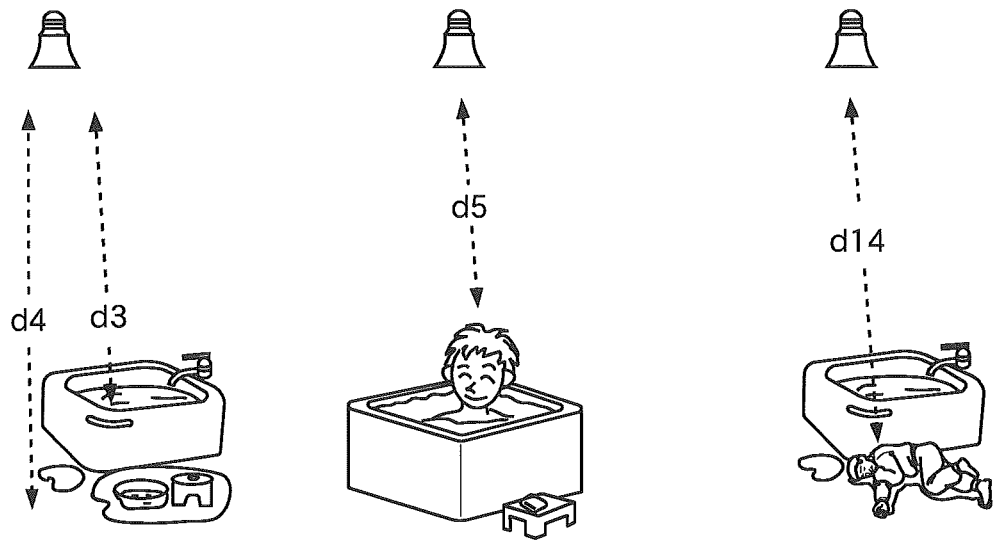
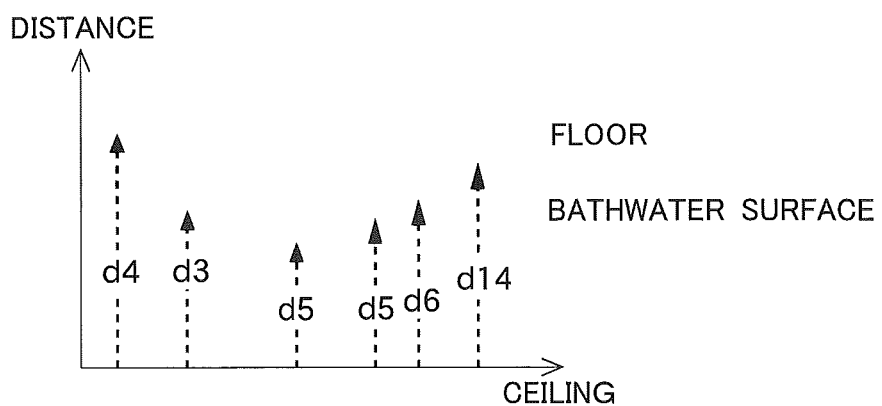
d4 = DISTANCE TO FLOOR SURFACE
d3 = DISTANCE TO THE BATHWATER SURFACE
d2 = DISTANCE TO HEAD WHEN SOAKING IN THE BATH
d14 = BELOW BATH SURFACE

FIG. 20B

| | | | RESPIRATORY ARREST | RESPIRATION STANDSTILL /SLEEP APNEA SYNDROME |
|---|---|---|---|---|
| ABNORMAL RESPIRATION AMOUNT | ABNORMAL NUMBER OF RESPIRATORIES | REDUCED | BRADYPNEA (NINE RESPIRATIONS PER MINUTE OR LESS) | |
| | | INCREASED | TACHYPNEA (25 RESPIRATIONS PER MINUTE OR MORE) | |
| | ABNORMAL TIDAL VOLUME | REDUCED | HYPOPNEA (HYPOVENTILATION) | SEE TABLE 2 |
| | | INCREASED | HYPERPNEA (HYPERVENTILATION) | SEE TABLE 3 |
| RESPIRATORY RHYTHM | PERIODIC ABNORMALITY | | CHEYNE-STOKES RESPIRATION | BRAIN DISEASE, CARDIAC FAILURE UREMIA, INTOXICATION, TERMINAL DISEASES |
| | IRREGULAR ABNORMALITY | | CONTINUOUS INSPIRATORY BREATHING | VASCULAR DISORDER OF THE CENTRAL NERVOUS SYSTEM, TUMOR, INFLAMMATION, INJURED (DISORDER PARTICULARLY ON THE PONTO-MEDULLARY LEVEL) |
| | | | INTERMITTENT RESPIRATION | |
| | | | PANTING (RESPIRATION WITH LOWER JAW MOVEMENT) | |
| | | | ATAXIC RESPIRATION (BIOT'S RESPIRATION) | |
| OTHER | ABNORMALITY OF PHYSICAL STATUS | | ORTHOPNEA | CARDIAC FAILURE, UREMIA |

FIG. 21
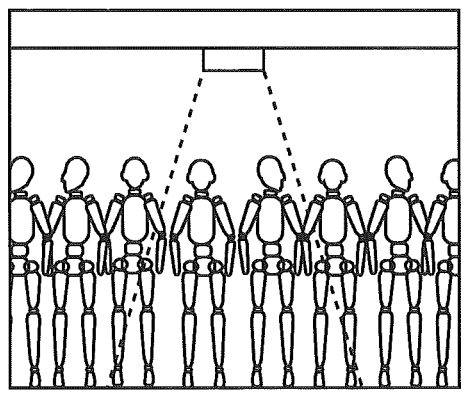
(a)
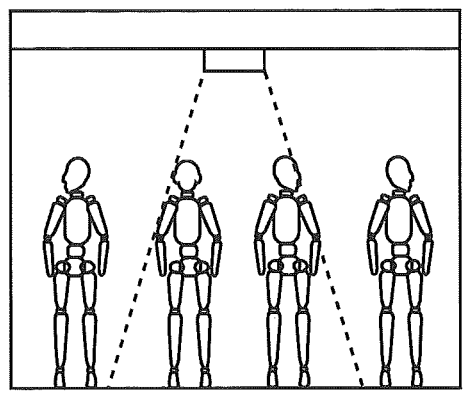
(b)
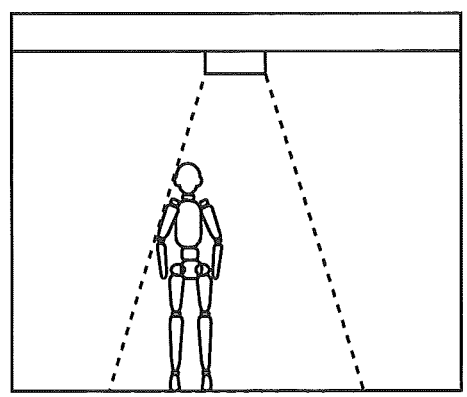
(c)

FIG. 22
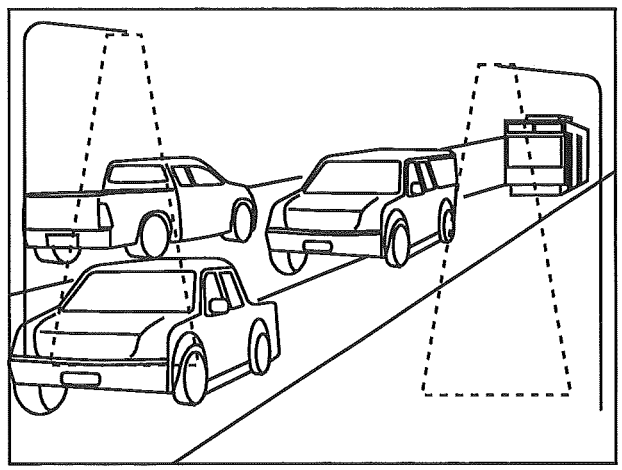
(a)
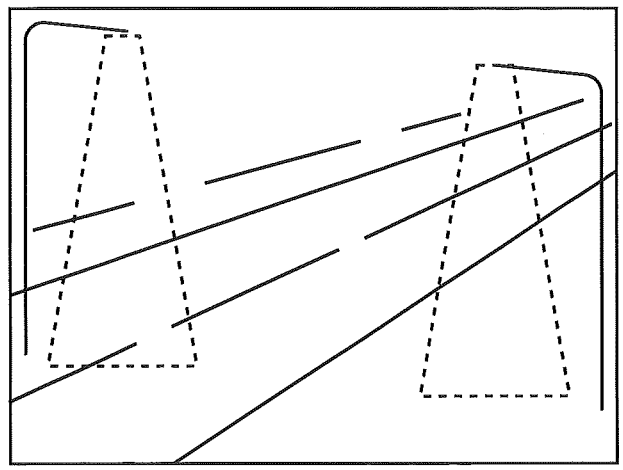
(b)

DEVICE FOR SENSING HUMAN BODY ABNORMALITY BY STANDING-WAVE RADAR AND METHOD FOR USING SAME

TECHNICAL FIELD

The present invention relates to a light-emitting diode (LED) illumination apparatus, and more particularly relates to a device for sensing human body abnormality using standing-wave radar provided with a function for sensing a danger situation of a human body positioned below an illumination apparatus using a standing-wave radar, and to a method for using same.

BACKGROUND ART

A conventional illumination apparatus for sensing a human body senses a human body using an infrared sensor, an ultrasonic sensor or Doppler sensor, and controls the on and off state of illumination (Patent Documents 4 and 5), but cannot sense a danger situation of a human body.

Patent Document 1 discloses a system having a radio wave sensor for emitting radio waves and for receiving reflected waves thereof, a detector for detecting the phase and amplitude of signals received by the radio wave sensor to obtain detection signals, and a signal processor for measuring the current position, movement, respiratory rate, and heart rate of an animal or resident from the detection signal to determine the presence of an animal or resident, the system being used as resident monitoring system that can be readily installed in residences to be monitored having a variety of floor plans, and that is capable of readily ascertaining the behavior dynamics of residents and changes in the living space.

Patent Document 2 discloses a non-contact cardiopulmonary function monitoring device provided with a radio wave sensor for detecting the movements of a monitored object using the Doppler effect, wherein movement signals are passed through a respiratory rate filter in which the frequency band of a respiratory rate is used as a pass frequency band, and are passed through a heart rate filter in which the frequency band of a heart rate is used as a pass frequency band, and the respiratory rate and heart rate are calculated from the maximum amplitude in each pass frequency band.

Furthermore, Patent Document 3 discloses a monitoring system for transmitting and receiving radio waves in a residence, extracting a respiration signal in a frequency band corresponding to the respiration of a resident and a movement signal in a higher frequency band than the respiration signal, from a signal that corresponds to a reflected wave received by a radio wave sensor, and determining that the resident is in an abnormal state when the resident has not moved for a fixed length of time or longer, on the basis of the movement signal, while the respiratory signal is detected (claim 1). Also, the radio wave sensor is a Doppler sensor (claim 3).

Patent Document 1: Japanese Laid-open Patent Application No. 2010-66877
Patent Document 2: Japanese Patent No. 3057438
Patent Document 3: Japanese Laid-open Patent Application No. 2006-285795
Patent Document 4: Japanese Laid-open Patent Application No. 2011-34938
Patent Document 5: Japanese Laid-open Patent Application No. 2003-132704

DISCLOSURE OF THE INVENTION

Problems the Invention is Intended to Solve

However, the conventional technique described in Patent Document 1 detects respiratory rate and heart rate of a person from the phase or amplitude detected by a plurality of radio wave sensors installed in each room (paragraph [0007]), but in relation to the position information of a resident, this conventional technique merely determines the position of a resident by assuming a resident is positioned in an area monitored by a sensor in which the phase or amplitude is fluctuating, and that a resident is not present in an area monitored by a sensor in which the phase or amplitude is not fluctuating (paragraph [0013]). In this manner, in relation to the position of a resident, only position information about which room a resident is in can be detected in Patent Document 1. In relation to an abnormality of a resident, an abnormality is determined in the case that the resident is in a location for a long period of time that the resident does not ordinarily remain for a long period of time (paragraph [0026]). Therefore, an abnormality of a person cannot be rapidly detected with high precision in Patent Document 1.

In the case that the amplitude and phase of a received signal of a reflected wave of an emitted radio wave are to be detected in accordance with Patent Document 1, the distance at which the amplitude and phase of the radio wave can be detected must be several meters or more away, and only the amplitude and phase of reflected waves from the position several meters or more away can be detected. When the detector is a Doppler radar, the heart rate and respiratory rate can be detected at a close distance, but a Doppler radar detects changed in the frequency of reflected waves, and the heart rate and respiratory rate cannot therefore be detected using only changes in the amplitude and phase of a signal, as is the case in Patent Document 1.

Furthermore, in Patent Documents 2 and 3, the frequency of the maximum amplitude is calculated from a signal detected using the Doppler effect as the respiratory rate and the heart rate, but since this is a Doppler scheme, the speed of an object can be detected, but the distance cannot be detected. Consequently, Patent Documents 2 and 3 cannot detect the position of a human body.

The present invention was devised in view of these problems, and an object thereof is to provide a device for sensing a human body abnormality using standing-wave radar and a method for using the same, which are capable of detecting the position of a human body, and the respiratory rate, heart rate, and the like thereof, and rapidly sensing sudden changes to the condition of the detected human body, by merely installing the present invention in lieu of existing illumination apparatuses installed in restrooms, bathing rooms, corridors, and the like.

Means for Solving the Problems

The device for detecting human body abnormality using standing-wave radar according to the present invention comprises:

a standing-wave sensor for externally transmitting a frequency-swept radio wave, detecting, at two points separated by a fixed distance, a reflected wave received from an external reflection object based on the transmitted wavelength with λ being the wavelength of the transmitted wave, and sensing a standing wave combined from the transmitted wave and the received wave;

a computation unit for removing the DC component from the intensity distribution of the frequency of the combined wave sensed by the standing-wave sensor, performing a Fourier transform, obtaining a distance spectrum, and computing a change in phase and distance to the reflection object;

a signal processor for removing the distance component obtained when no person is present in a measurement space from the distance component to the obtained reflection object, and obtaining distance information that is different from the distance component obtained when no person is present in the measurement space to extract the distance component to a person to be measured who has entered into the measurement space; and a determination unit for sensing an abnormality in a person to be measured from a variation in the intensity distribution of the component associated with the distance to the person to be measured and determining the physical state of the person to be measured and the physiological state including a respiratory rate and pulse from the change in phase.

The device for detecting human body abnormality using standing-wave radar according to the present invention comprises:

a standing-wave sensor for externally transmitting a frequency-swept radio wave, detecting, at two points separated by a fixed distance, a reflected wave received from an external reflection object based on the transmitted wavelength with $\lambda$ being the wavelength of the transmitted wave, and sensing a standing wave combined from the transmitted wave and the received wave;

a computation unit for removing the DC component from the intensity distribution of the frequency of the combined wave sensed by the standing-wave sensor, performing a Fourier transform, obtaining a distance spectrum, and computing from the distance spectrum of a first interval and the distance spectrum of a second interval in a single period a phase difference from two distance spectra and a change in phase;

a signal processor for removing the distance component obtained when no person is present in a measurement space from the distance component to the reflection object obtained from the phase difference, and obtaining distance information that is different from the distance component obtained when no person is present in the measurement space to extract the distance component to a person to be measured who has entered into the measurement space; and a determination unit for sensing an abnormality in a person to be measured from a variation in the intensity distribution of the component associated with the distance to the person to be measured and determining the physical state of the person to be measured and the physiological state including a respiratory rate and pulse from the change in phase.

The standing-wave radar-integrated LED illumination apparatus of the present invention, wherein, e.g., a power supply unit composed of a connector that can be mounted in a light bulb socket or sealing is disposed below the case, and power is supplied to the LED light source and the standing-wave sensor via the power supply unit.

The standing-wave radar-integrated LED illumination apparatus of the present invention, wherein, e.g., the computation unit, the signal processor, and the determination unit are housed in the case as a module together with the standing-wave sensor.

Furthermore, in the standing-wave radar-integrated LED illumination apparatus of the present invention, e.g., the determination unit emits an alarm by transmitting an alarm signal to an external alarm signal receiver when the distance to the person to be measured, or the respiratory rate or pulse of the person to be measured has been determined to be in a danger area set in advance.

In the method for using the standing-wave radar-integrated LED illumination apparatus of the present invention, the standing-wave radar-integrated LED illumination apparatus of the present invention described above is installed in a ceiling of a building or residence to determine an abnormality of a human body inside the residence or building.

In the method for using the standing-wave radar-integrated LED illumination apparatus of the present invention, the standing-wave radar-integrated LED illumination apparatus described above is installed in a ceiling of a vehicle or a ceiling of passage or tunnel to determine congestion of human bodies therein.

In the method for using the standing-wave radar-integrated LED illumination apparatus of the present invention, the standing-wave radar-integrated LED illumination apparatus described above is installed for illuminating a road, and a water level of water that has flooded a road and congestion of human bodies positioned in the road are determined.

Effects of the Invention

According to the present invention, it is possible to measure with high precision the distance to a person being measured from a very small distance to a distant location and to measure the respiratory rate, pulse, and other very small displacements of a person being measured, by analyzing standing waves.

BRIEF DESCRIPTION OF THE DRAWINGS

FIG. 18 represents the usage method when the LED illumination apparatus of an embodiment of the present invention has been installed in a bathing room;

FIG. 20A and FIG. 20B represent a typical abnormal respiratory pattern;

FIG. 21 represents the state in which the LED illumination apparatus of an embodiment of the present invention is used for monitoring the interior of a passenger train;

FIG. 22 represents the state in which the LED illumination apparatus of an embodiment of the present invention is used for monitoring road conditions;

BEST MODE FOR CARRYING OUT THE INVENTION

Figure 1:
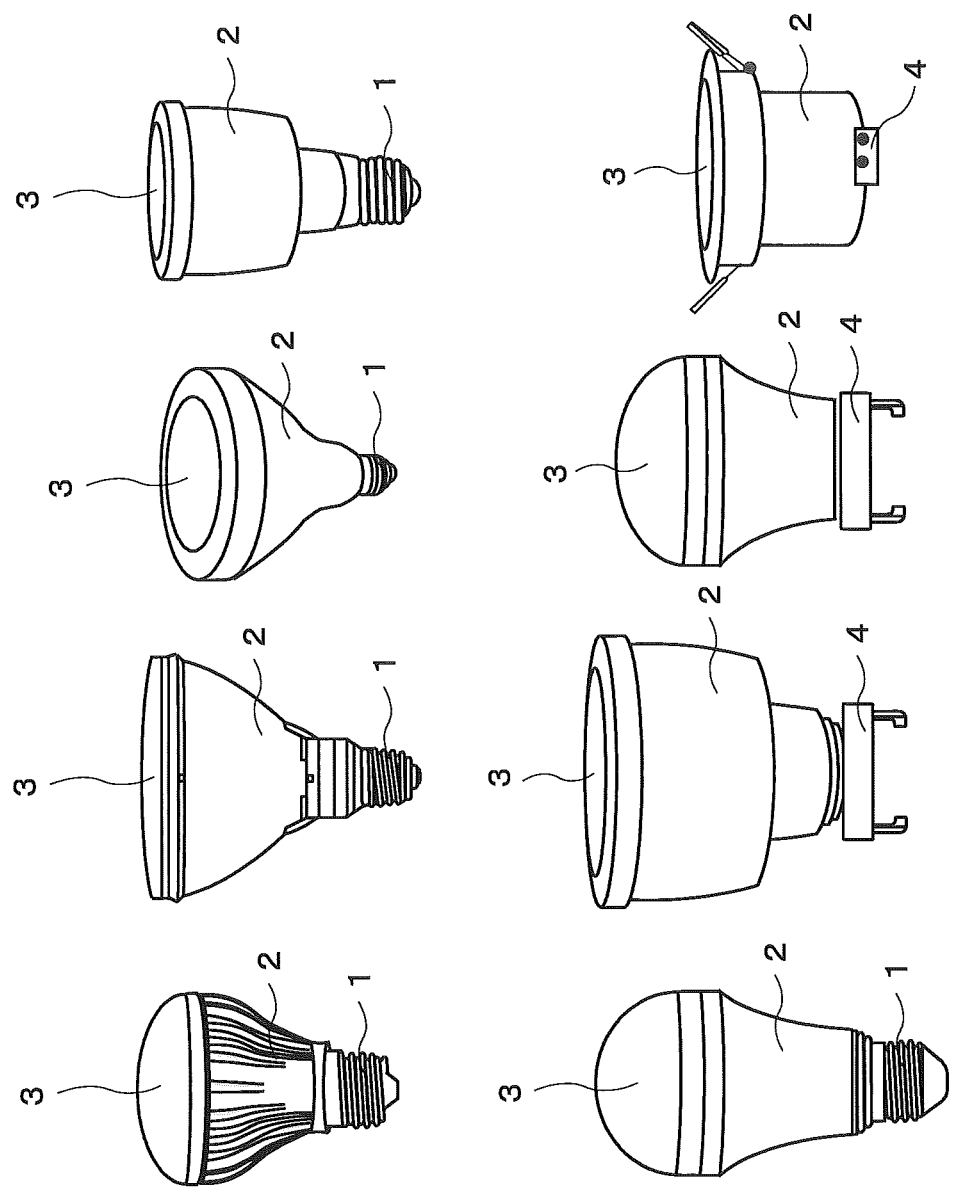
FIG. 1 is a view of the external appearance of the LED illumination apparatus according to embodiments of the present invention.

Next, embodiments of the present invention will be described in detail with reference to the attached drawings. FIG. 1 is a view of the external appearance of the standing-wave radar-integrated LED illumination apparatus according to embodiments of the present invention. A case of the LED illumination apparatus is composed of: a metal cap 1 that can be mounted in an existing socket; a case main body 2 having a heat-dissipating function and being formed from ABS or another resin material, or an aluminum material or the like; and a translucent cover 3 composed of a transparent or semi-transparent ABS or polycarbonate or the like translucent resin material, or glass or the like. The translucent cover 3 has a lens shape for scattering light or narrowing a light beam. In lieu of a metal cap 1, some illumination apparatuses have a hook sealing 4 for hooking and mounting on the sealing of a ceiling. In this manner, there are numerous LED illumination apparatuses, and the present invention can be applied to any LED illumination apparatus.

Figure 2:
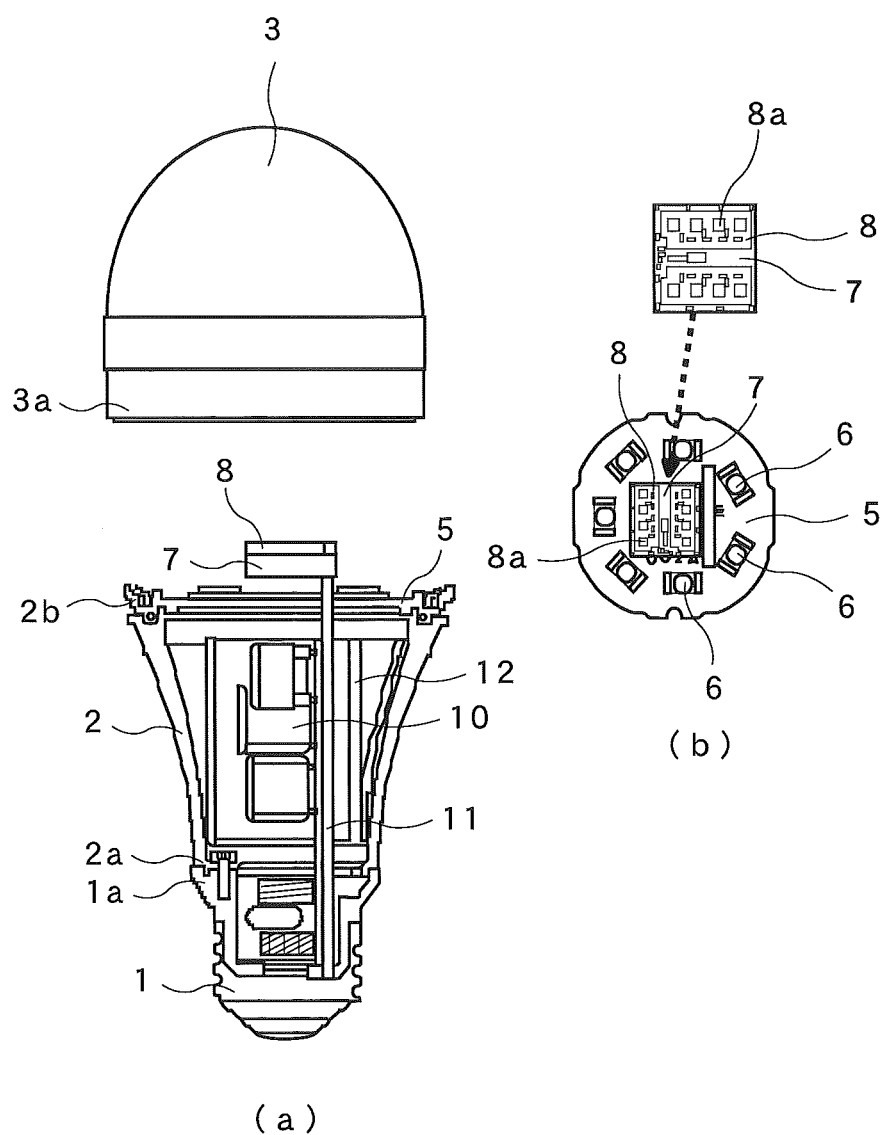
FIG. 2 is a longitudinal sectional view the same showing the structure thereof.

FIG. 2 represents the structure of an LED illumination apparatus according to an embodiment of the present invention. In the LED illumination apparatus, a surface-mounted LED 6, a standing-wave radar module 8, and a LED control unit 10 are accommodated inside a case composed of the metal cap 1, the case main body 2, and the cover 3. The lower half portion of the metal cap 1 is threadably inserted into a socket and is formed from an electroconductive material. The upper half portion of the metal cap 1 is an insulating support body. A threaded part 1a is provided to the upper end part of the insulating support body of the metal cap 1, the threaded part 1a being extended along the inner peripheral edge part thereof in peripheral direction. A threaded part 2a is also provided to the upper end part of the case main body 2, the threaded part 2a being extended along the outer peripheral edge part thereof in peripheral direction. The threaded part 1a is screwed onto the threaded part 2a, whereby the metal cap 1 and the case main body 2 are coupled together. Also, a threaded part 2b is formed on the upper part of the case main body 2, a threaded part 3a is formed in the lower end part of the cover 3, and the threaded part 3a is screwed onto the threaded part 2b, whereby the cover 3 and the case main body 2 are coupled together.

An insulating guide frame 12 for securing a board is disposed inside the case main body 2, and a board 11 of the LED control unit 10 is secured to the guide frame 12. The board 11 is secured to the guide frame 12 such that the surface thereof is in the vertical direction, i.e., such that the surface of the board 11 is parallel to the center axis of the illumination apparatus. The LED control unit 10 is mounted on the board 11 and is arranged within the space enclosed by the case main body 2 and the metal cap 1. An externally supplied 100-V AC power is fed to the board 11 inside the metal cap 1, and the power is AC-DC converted by a converter mounted on the board 11, and is thereafter fed to the LED control unit 10.

An aluminum board 5 having excellent heat dissipation is arranged with the surface thereof horizontal on the upper end part of the case main body 2. The aluminum board 5 is supported by the edge part of the upper end part of the case main body 2, and the board 11 is inserted through the aluminum board 5 so as to protrude into the cover 3 area. The radar control module board 7 is supported with the surface thereof horizontal on the upper end part of the board 11, and the standing-wave radar module 8 is mounted on the radar control module board 7. A plurality (seven in the illustrated example) of LEDs 6 is arranged in positions equivalently distributed about the center axis of the illumination apparatus, i.e., in positions of equidistant intervals at the outer periphery. Wiring for the board 11 is connected to the power line of the aluminum board 5, the LEDs 6 mounted on the aluminum board 5 are supplied with power by the LED control unit 10 via the wiring for the board 11 to cause the LEDs 6 to emit light. Power is supplied via the board 11 to the standing-wave radar module 8 mounted on the radar control module board 7. The standing-wave radar module 8 transmits/receives microwaves or other radio waves, and the radar control module board 7 wirelessly transmits detection signals to an external relay apparatus. An antenna 8a is disposed on the upper surface of the standing-wave radar module 8, and radio waves are transmitted/received via the antenna 8a. The standing-wave radar module 8 is capable of being inclined in relation to the radar control module board 7, and the standing-wave radar module 8 is inclined to thereby allow the orientation of the antenna 8a to be adjusted.

Figure 3:
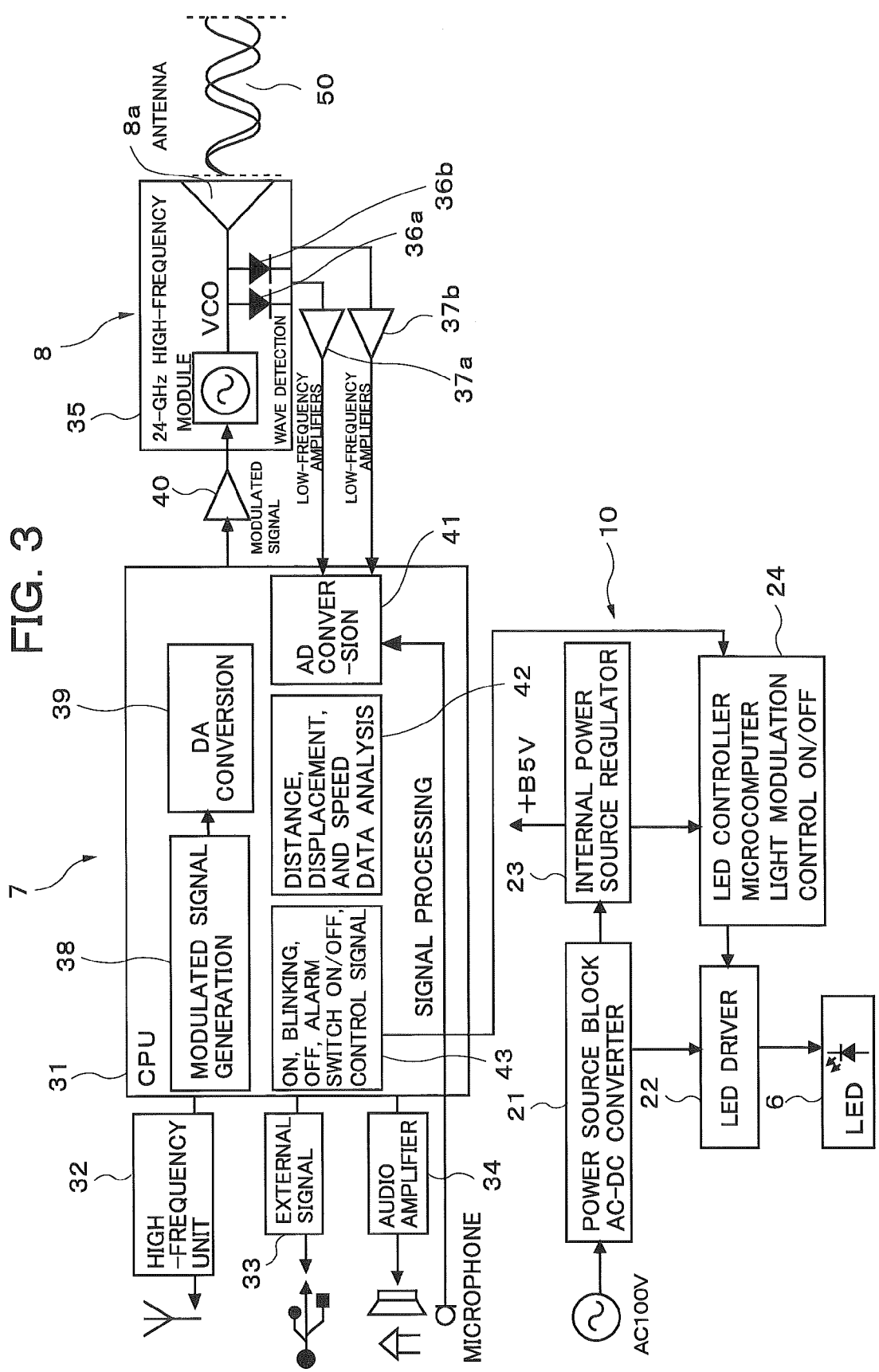
FIG. 3 is a block diagram of the radar control module board 7, the standing-wave radar module 8, and the LED control unit 10 of the same.

FIG. 3 is a block diagram of the radar control module board 7, the standing-wave radar module 8, and the LED control unit 10. AC power at 100 V is inputted from an external power source to a power supply block 21 of the LED control unit 10, converted to DC power by an AC-DC converter of the power supply block 21, and inputted to an internal power regulator 23. A DC 5-V power is fed to the standing-wave radar module 8 and a LED controller microcomputer 24. The output of the AC-DC converter is fed to a LED driver 22 as well and used for driving the LEDs 6. The LED controller microcomputer 24 receives control signals from the standing-wave radar module 8, and outputs a LED on/off control signal and a light modulation control signal to the LED driver 22. The LED driver 22 drives the LEDs 6 on the basis of these control signals.

A computation unit 31 is provided to the radar control module board 7. The computation unit 31 generates a frequency control voltage that has been FM-modulated by a modulation signal generator 38, the frequency control voltage is inputted to the control input of the VCO of a 24-GHz high-frequency module 35 after the frequency control signal converted to an analog signal by a DA converter 39 has been amplified via an operational amplifier 40. The VCO is made to sweep the frequency of the emitted radio wave by the frequency control signal.

The 24-GHz high-frequency transceiver 35 is provided to the standing-wave radar module 8. The 24-GHz high-frequency transceiver 35 is a module in which a 24-GHz band VCO (voltage control oscillator) and flat antenna 8a have been integrated. With this transceiver 35, microwaves are emitted from the flat antenna 8a via the VCO and the reflected waves from the reflected body are detected by the antenna 8a. Two wave detectors 36a, 36b are housed in the transceiver 35, and the wave detectors 36a, 36b detect transmitted waves and received waves.

When radio waves are transmitted from the antenna 8a and a reflection object is present, reflected waves return to the antenna 8a and superimposed waves having the same frequency yet different travel directions result in a standing wave. A transmitted signal (traveling wave) and a received signal (reflected wave) are exist together in the antenna power supply unit and in the pathway connecting the VCO and antenna 8a, and these signals combined produce a standing wave. In this case, the sweep voltage fed to the VCO must be held constant at least during the time that the emitted radio wave is reflected from the reflection object and returns. Therefore, the sweep voltage must be varied in a stepwise fashion. The VCO is controlled so as to sequentially switch the frequency, whereby the signal level of mixed waves for a plurality of frequencies is detected by the wave detectors 36a, 36b. The power of the transmitted waves, the power of the reflected waves, and a component produced by the standing wave are detected by the wave detectors 36a, 36b. The resulting detected-wave signals are amplified in the required frequency band of 400 kHz or less by the operational amplifiers 37a, 37b, are converted to a digital signal by an AD converter 41 inside the computation unit 31, and are thereafter inputted to a signal processor 42. The inputted signals have a period that is inversely proportional to the distance from the reflection object and are therefore made to undergo a Fourier transform in the signal processor 42 to thereby obtain a frequency which is the reciprocal of the period, whereby the distance to a reflection object can be obtained. Information about very small displacements of a reflection object can be detected on the basis of the phase of the resulting waveform. For example, in the case of 24 GHz, a very small displacement is a value obtained by dividing the speed of light by $4\pi f$, and displacements in the range of about ±3.125 mm can be detected. In this manner, the signals detected by the wave detectors 36a, 36b are made to undergo signal processing, the distance from the reflection object and the speed and displacement of the reflection object are computed, and chronological changes thereof are measured, whereby movement of the reflection object can be detected. The movement of the reflection object is analyzed by the computation unit 42, the results are outputted to an alarm unit 43, the alarm unit 43 outputs to the LED controller microcomputer 24 a control signal that causes LEDs to switch on, blink, switch off, causes an alarm to switch on and off, or causes another action.

The computation unit 31 transmits the obtained state of the reflection object to the exterior, wirelessly via a high-frequency unit 32 and wired by a output terminal 33. Also, the computation unit 31 emits an alarm sound via an audio amplifier 34. Any means among wireless transmission, wired transmission, and alarm sound may be used.

Figure 4:
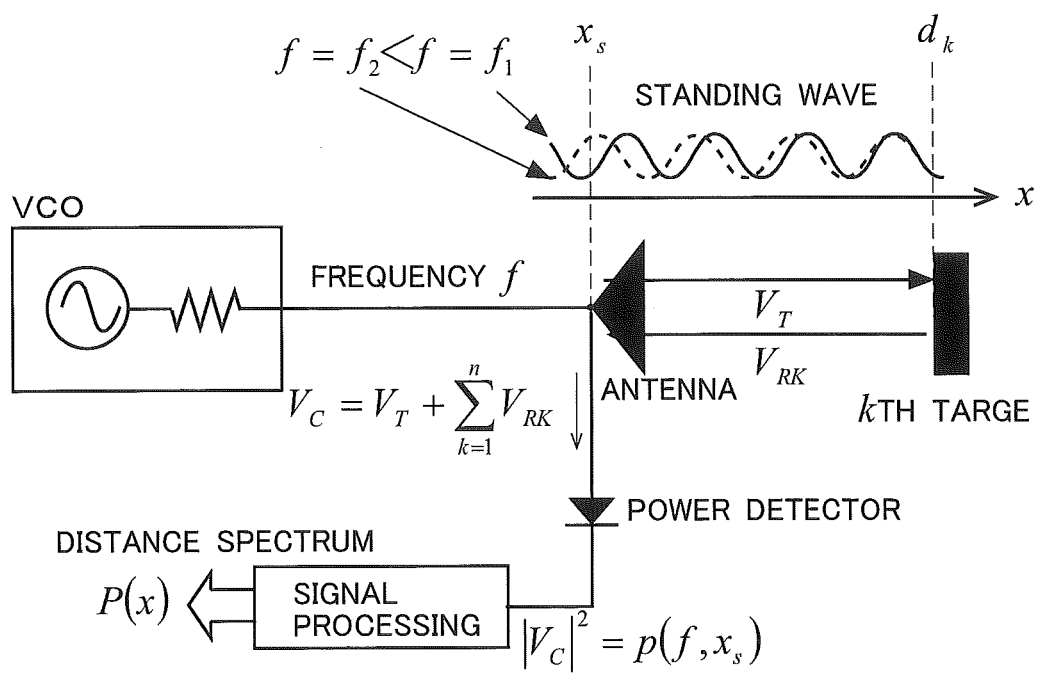
FIG. 4 represents the basic configuration of a standing-wave radar.

Next, the operation of an embodiment of the present invention will be described together with the configuration of the signal processor 42. A standing wave is produced by interference between a transmitted wave VT generated from the VCO, which is the signal source, and reflected waves VR1, VR2, VR3, ..., VRn from a target, as shown in FIG. 4. The standing-wave radar senses the existence of a target by using this standing wave, and measures the distance d1, d2, d3, ..., do to the target.

Figure 5:
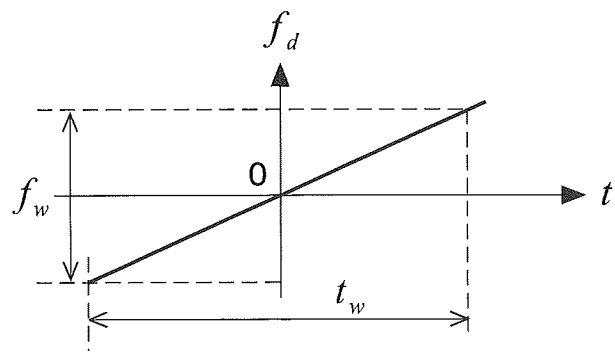
FIG. 5 represents wavelength of a transmitted wave.

The transmitted wave (traveling wave) is represented by Formula 1, where A is the amplitude of the signal source, f is the frequency, and c is the speed of light ($3 \times 10^8$ m/s). However, the frequency f is represented by f0 and fd, as shown in FIG. 5.

$$V_T = Ae^{j2\pi} \int f\left(t - \frac{x}{c}\right) d\left(t - \frac{x}{c}\right)$$ [Formula 1]

The reflected wave from the target can be represented by Formula 2 below, where dk is the distance to the kth target, γk (magnitude of the reflection coefficient) is the ratio of the magnitude of the reflected wave with respect to the transmitted wave at an arbitrary point on the x axis, and φk (phase of the reflection coefficient) is the phase difference.

$$V_{Rk} = A\gamma_k e^{j\phi_k} e^{j2\pi} \int f\left(t - \frac{2d - x}{c}\right) d\left(t - \frac{2d - x}{c}\right)$$ [Formula 2]

The detection wave output detected by the antenna results in a combined wave, and the amplitude Vc is therefore represented by Formula 3 below. The power is the square of the amplitude, and the power of the combined wave is therefore represented by Formula 4 below.

$$V_C = V_T + \sum_{k=1}^{n} V_{Rk}$$ [Formula 3]

$$p(f_d, x) = \left| V_T + \sum_{k=1}^{n} V_{Rk} \right|^2$$ [Formula 4]

The magnitude of the transmitted wave is greater than the magnitude of the reflected wave by a magnitude of one, where γk is considerably less than 1. In view of this fact, Formula 1 and Formula 2 are substituted into Formula 4 to obtain an approximated value, resulting in Formula 5.

$$p(f_d, x_s) \approx A^2 \left\{ 1 + \sum_{k=1}^{n} \gamma_k^2 + 2\sum_{k=1}^{n} \gamma_k \cos\left( \frac{4\pi f_d}{c}(d_k - x_s) + \frac{4\pi f_0}{c}(d_k - x_s) - \phi_k \right) \right\}$$ [Formula 5]

In Formula 5, the first term in the brackets ({ }) represents the power of the transmitted wave, the second term represents the power of the reflected wave, and the third term represents the change in power by the standing wave. A conventional radar receives a reflected wave, which is the second term, and performs signal processing, but in the present invention, the signal of the third term undergoes signal processing. Consequently, since the first and second terms are to be deleted, the combined wave power p(fd, xs) is differentiated by fd, and the first and second terms are deleted.

Figure 6:
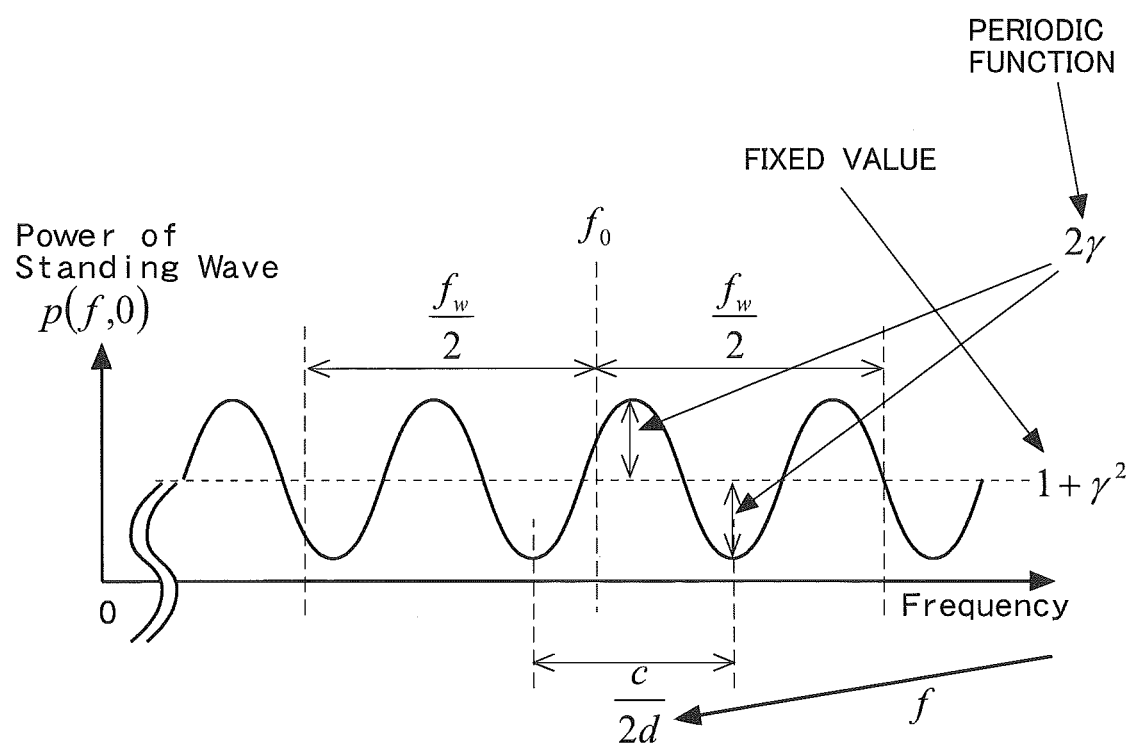
FIG. 6 represents the power of a combined wave.
Figure 7:
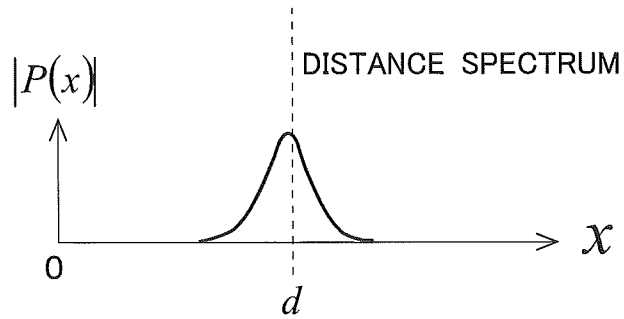
FIG. 7 is a view of post Fourier conversion.

Here, when the number of targets (reflection objects) is 1, n=1 is substituted into Formula 5 to obtain Formula 6 below. FIG. 6 is a result of forming a graph based on Formula 6. In other words, the power of the combined wave is the sum of a fixed value $1+\gamma^2$ and the periodic function. In FIG. 6, the frequency (reciprocal of the period) of the periodic function is c/2d, which give consideration to the distance d component. Consequently, obtaining the frequency from the period results in obtaining the distance d. The DC component $1+\gamma^2$ is removed from Formula 6 and a Fourier transform is carried out, whereupon a distance spectrum P(x) is obtained, as shown in FIG. 7.

$$p(f, 0) = 1 + \gamma^2 + 2\gamma\cos\left(2\pi\frac{2d}{c}f - \Phi\right) \quad \text{[Formula 6]}$$

First, the variables are substituted in the Fourier transform formula shown in Formula 7 below and a Fourier transform is carried out using the observation position as the origin to thereby obtain the distance spectrum shown in Formula 8 below. In the formula, $Sa(z)=\sin(z)/z$. In Formula 8, the DC portion has not be cut. When a function having a period is Fourier-expanded, it is broken down into oscillation components (sin, cos) and the DC component included in the function. In terms of a formula, the distance spectrum is displayed in the manner shown in Formula 8 below.

Fourier transform formula $F(\omega) = \int_{-\infty}^{\infty} f(t)e^{-j\omega t}dt$    [Formula 7]

Variable substitution $t \dashrightarrow f_d$ $\frac{\omega}{2\pi} \dashrightarrow \frac{2x}{c}$ $f(t) \dashrightarrow p(f_d, x_s)$ Let the observation position be the origin $\dashrightarrow x_s = 0$ $$P(x) = \int_{-f_W/2}^{+f_W/2} p(f_d, 0)e^{-j\frac{4\pi x f_d}{c}}df_d = \quad \text{[Formula 8]}$$

$$A^2 f_W \left\{ \begin{array}{l} \left(1 + \sum_{k=1}^{n} \gamma_k^2\right) Sa\left(\frac{2\pi f_W}{c}x\right) + \\ \sum_{k=1}^{n} \gamma_k e^{-j\phi_k} e^{-j\frac{4\pi f_0 d_k}{c}} Sa\left(\frac{2\pi f_W}{c}(x - d_k)\right) + \\ \sum_{k=1}^{n} \gamma_k e^{j\phi_k} e^{-j\frac{4\pi f_0 d_k}{c}} Sa\left(\frac{2\pi f_W}{c}(x + d_k)\right) \end{array} \right\}$$

$A^2 f_w(1+\Sigma\gamma_k^2)Sa(2\pi f_w/c)x)$ in Formula 8 is the DC component, and this DC component is removed by a capacitor in a real circuit.

Figure 8:
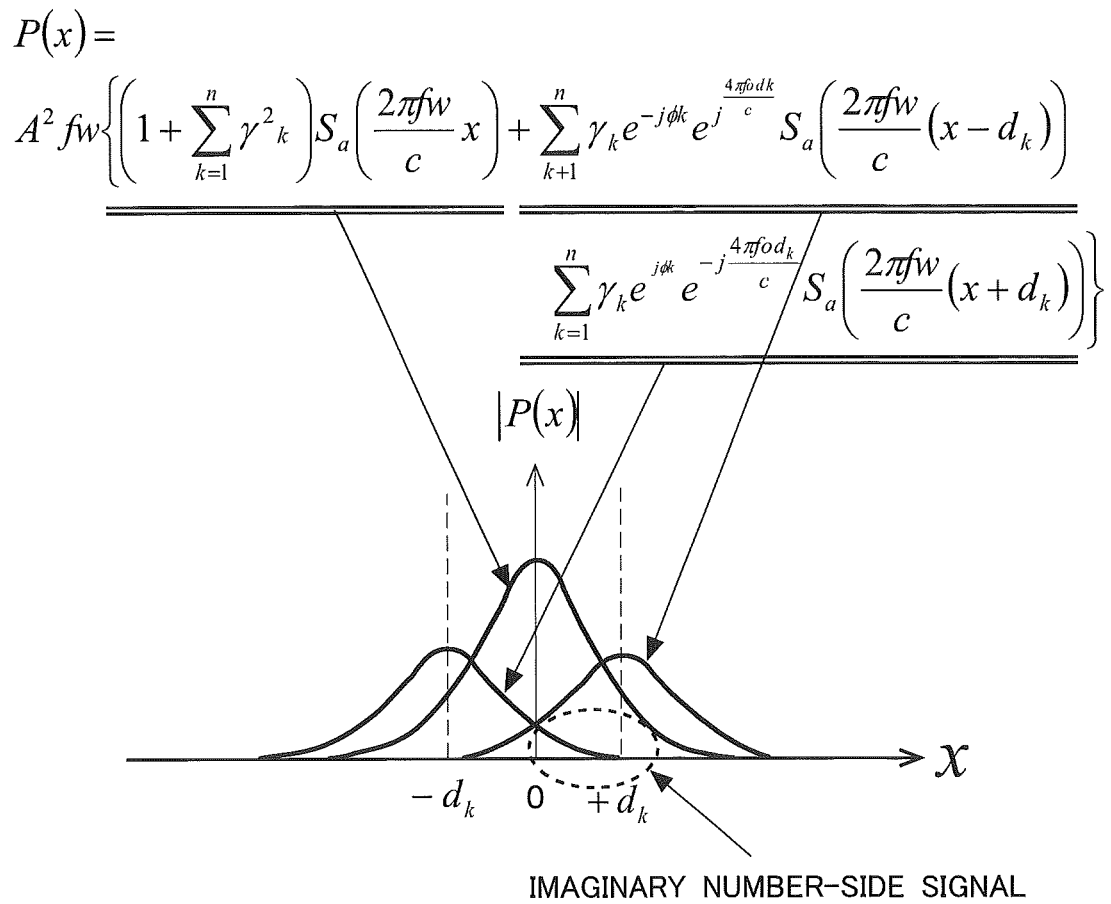
FIG. 8 represents the power of a combined wave.

FIG. 8 shows the case in which the power $P(x)$ represented by the third expression in Formula 8 is viewed in a graph. The DC component, which is the first term in the brackets ({ }) in Formula 8, is removed, the cos component, which is the third term, is converted to a complex sinusoidal wave (analysis signal) and removed, and the component of the second term, which is the standing wave component, can be extracted out. However, a signal on the imaginary number side leaks into the second term component in the braces ("{ }") of Formula 8, as shown by the broken line in FIG. 8. In other words, the standing wave component of this portion is a value in which a signal on the imaginary number side has leaked in.

Figure 9:
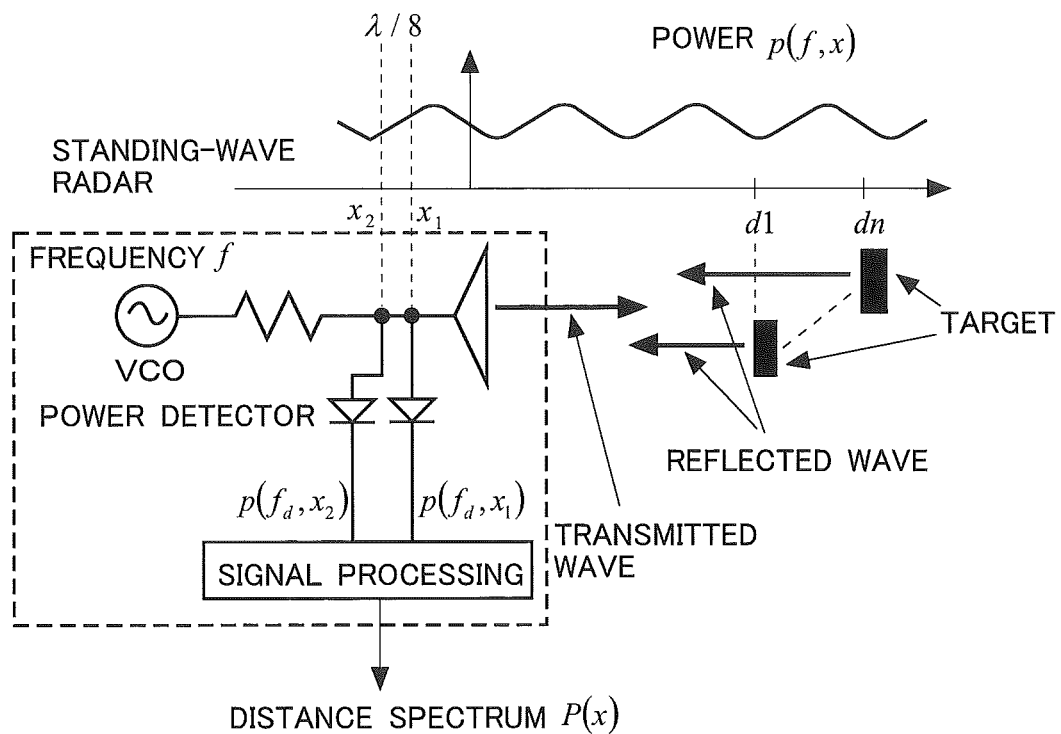
FIG. 9 represents the basic configuration of a standing-wave radar in relation to a plurality of targets.

In order to solve such problems, when signal obtained by combining the transmitted wave and the reflected wave is detected in the present invention, the signal level is detected at two points at a distance of $\lambda/8$ from each other, where $\lambda$ is the wavelength of the transmitted wave, as shown in FIG. 9. In other words, when the x axis is the travel direction of the radar, the antenna receives a reflected wave from n targets, which are the reflection objects (where n is a natural number; only two are shown). This is detected together with the transmitted wave by two power detectors set at a distance of $\lambda/8$ from each other in the x-axis direction, and this undergoes signal processing. At this point, the power of the detector positioned at $x_1=0$ is obtained as $p(f_d, 0)$ shown in Formula 9 below by substituting $x_1=x_s=0$ into Formula 5, which shows the detection power, and the power of the detector positioned at $x_1=-\lambda/8$ is obtained as $p(f_d, -\lambda/8)$ shown in Formula 9 below by substituting $x_2=x_s=-\lambda/8$ into Formula 5, which shows the detection power, where $p(f_d, x_1)$ and $p(f_d, x_2)$ are the power levels detected by the two detectors. As shown in Formula 9, a standing wave is detected as two points set at a distance of $\lambda/8$ from each other, whereby the orthogonal component of cos and sin is obtained in the standing-wave component outputted by the detector positioned at each (0, $-\lambda/8$), and it is thereby possible to remove the effect of the signal that has leaked in from the imaginary image side. In other words, this is an analysis signal obtained by a vector in which the orthogonal components of cos and sin (the X-axis component and the Y-axis component) have been combined. Ordinarily, a signal on the imaginary axis side cannot be measured, but the signal on the imaginary axis side can be measured at the $-\lambda/8$ position, and a vector combined signal can be formed. The rotational speed of this vector is the frequency, and therefore, in the present embodiment, this frequency and phase are analyzed.

Output of detector positioned at $X_1 = 0$    [Formula 9]

$p(f_d, 0) =$ $$A^2 \left\{ 1 + \sum_{k=1}^{n} \gamma_k^2 + 2\sum_{k=1}^{n} \gamma_k \cos\left(\frac{4\pi(f_0 + f_d)d_k}{c} - \phi_k\right) \right\}$$

Output of director positioned at $x_2 = -\frac{\lambda}{8}$ $\left(\text{where } \lambda = \frac{c}{f_0}\right)$ $p\left(f_d, -\frac{\lambda}{8}\right) =$ $$A^2 \left\{ 1 + \sum_{k=1}^{n} \gamma_k^2 - 2\sum_{k=1}^{n} \gamma_k \sin\left(\frac{4\pi(f_0 + f_d)d_k}{c} - \phi_k\right) \right\}$$

The terms a and b are given in Formula 10 below, where a is the standing-wave component of the output of the detector positioned at $x_s=0$ in Formula 9, and b is the standing-wave component of the output of the detector positioned at $x_s=-\lambda/8$. When the third expression in Formula 8 is substituted on the basis of Formula 11 below, Formula 12 and Formula 13 below are obtained. In other words, it is possible to perform the substitution such that the X axis and the Y axis (real signal, imaginary axis signal) obtained by Formula 10 are converted to a real signal. More precisely, Formula 13 expresses a signal in the time direction and a signal on the axis of rotation, but ultimately, it is apparent that a rotating analysis signal can be calculated using Formula 13.

$$a = \sum_{k=1}^{n} \gamma_k \cos\left(\frac{4\pi(f_0 + f_d)}{c}d_k - \phi_k\right) \quad \text{[Formula 10]}$$

$$b = \sum_{k=1}^{n} \gamma_k \sin\left(\frac{4\pi(f_0 + f_d)}{c}d_k - \phi_k\right)$$

-continued $$P_{DC} = A^2\left(1 + \sum_{k=1}^{n} \gamma_k^2\right)$$ [Formula 11]

$$m(f_d) = 2A^2\sqrt{a^2 + b^2}$$

$$\theta(f_d) = \arctan\left(\frac{b}{a}\right)$$

$$a = \sum_{k=1}^{n} \gamma_k \cos\left(\frac{4\pi(f_0 + f_d)}{c}d_k - \phi_k\right)$$

$$b = \sum_{k=1}^{n} \gamma_k \sin\left(\frac{4\pi(f_0 + f_d)}{c}d_k - \phi_k\right)$$

$$p(f_d, x_s) = P_{DC} + m(f_d)\cos\left(\theta(f_d) - \frac{4\pi(f_0 + f_d)}{c}x_s\right)$$ [Formula 12]

$$m(f_d)e^{j\theta(f_d)} = 2A^2(a + jb)$$ [Formula 13]

$$= 2A^2\left\{\sum_{k=1}^{n}\gamma_k\cos\left(\frac{4\pi(f_0 + f_d)}{c}d_k - \phi_k\right) + j\sum_{k=1}^{n}\gamma_k\sin\left(\frac{4\pi(f_0 + f_d)}{c}d_k - \phi_k\right)\right\}$$

$$= 2A^2\sum_{k=1}^{n}\gamma_k e^{j\left(\frac{4\pi(f_0+f_d)}{c}d_k - \phi_k\right)}$$

Figure 10:
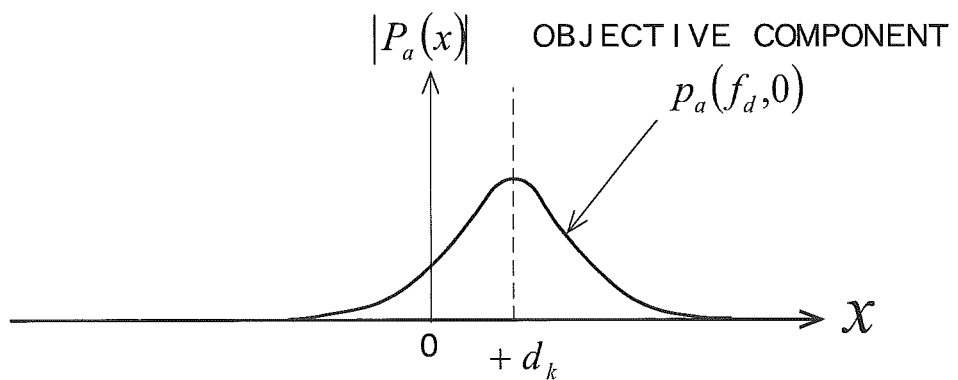
FIG. 10 is a spectral view showing the objective component pa (fd, 0)
Figure 12:
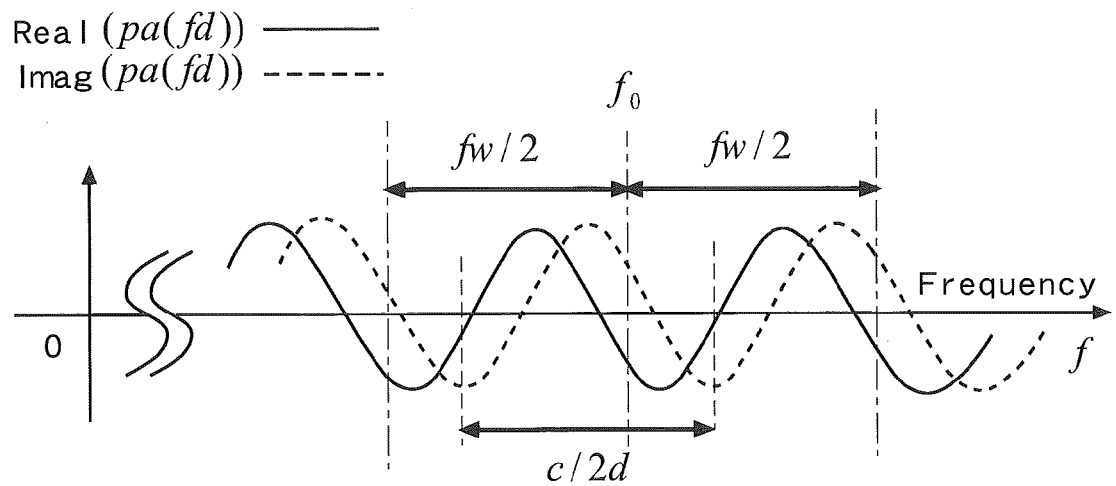
FIG. 12 represents the anti-logarithm portion and the imaginary number portion of the spectrum of a combined wave.

The term PDC on the right side of Formula 12 is the DC component, and $m(f_d)\cos(\theta(f_d)-4\pi(f_0+f_d)/c\cdot x_s)$ is the standing-wave component which varies in a periodic fashion. In relation to this standing-wave component, the combined component a+jb produced from the component a positioned at $x_s=0$ and the component b positioned at $x_s=-\lambda/8$ is the orthogonal component between sin and cos, as described above, and the analysis signal is a combination of a and b, whereby the effect of the unnecessary signal (the signal which has leaked in from the imaginary number side shown in FIG. 8) is removed. Accordingly, this value (the signal of Formula 13) is analyzed and the objective component $(f_d, 0)$ shown in FIG. 10 is thereby obtained. FIG. 12 shows the distance spectrum obtained by applying a Fourier analysis to the detection wave signal, and the fluctuation period f of the standing-wave power produced by sweeping the transmission frequency, i.e., the frequency f of the distance spectrum, is represented by c/(2d), as shown in FIG. 12. Accordingly, when the DC component is removed from the detected combined wave and subjected to a Fourier transform, the frequency f can be obtained and the distance d to a person being measured can be obtained.

Figure 13:
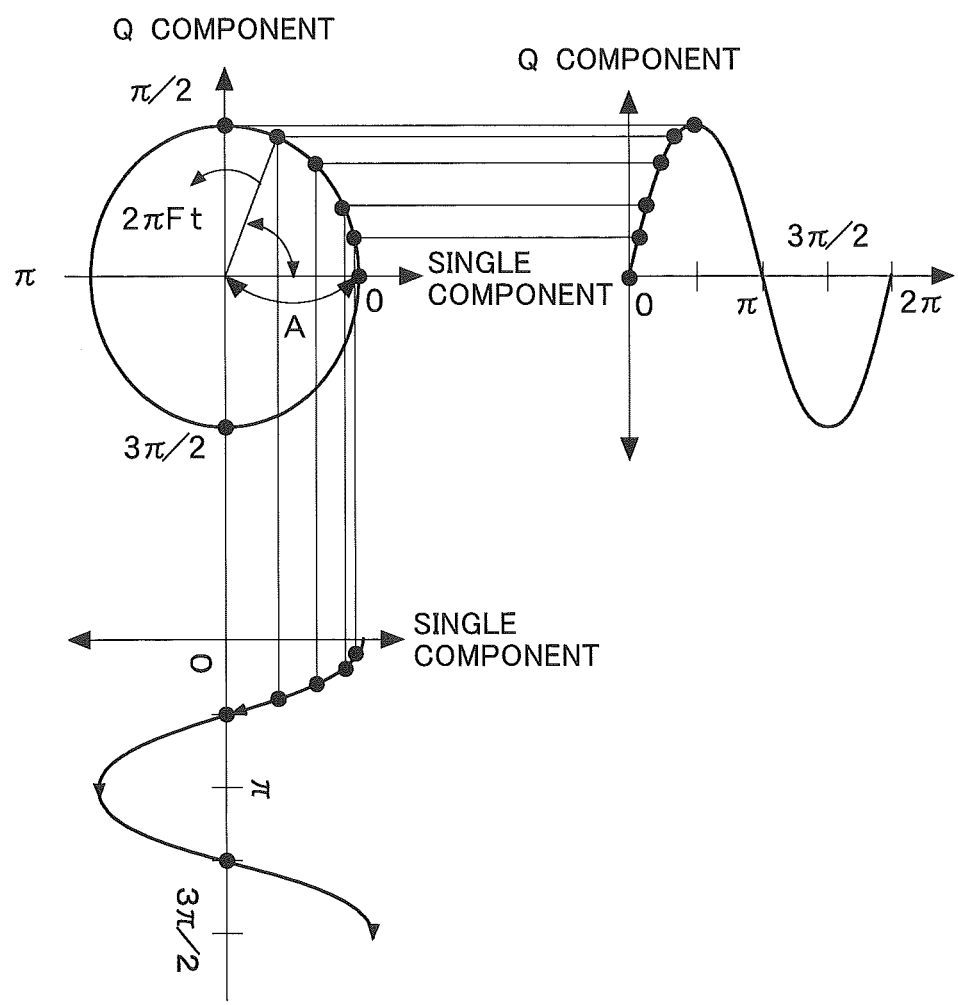
FIG. 13 illustrates the detection positions of a reflected wave.

In the description above, an analysis signal is a combination of a component a positioned at $x_s=0$ and a component b positioned at $x_s=-\lambda/8$, but the present invention is not limited thereby, and it is also possible to measure the distance between two points set at a distance from each other in the x-axis direction, multiply the signal obtained using the real axis and the imaginary axis by a coefficient to obtain a combined signal by calculation. The power level detected by the two detectors is manifest as the real-axis component (I component) and the imaginary-axis component (Q component), and each are an orthogonal component of a sin waveform and a cos waveform, as shown in FIG. 13. At this point, when the detection position of the reflected wave is set at a distance of $\lambda/8$ away in the x-axis direction, the phase $\Phi$ is 45° and the signals obtained on the real axis and the imaginary axis are in a 1:1 relationship. Therefore, it is possible to dispense with a coefficient and perform the analysis directly. However, when the distance between the two points is, e.g., $\lambda/6$, the phase is 60°, and the distance can be analyzed using a coefficient with the real axis (x axis) and the imaginary axis (y axis) in a 1:2 relationship (the imaginary axis being double the real axis). Accordingly, computation is not necessarily limited to the case in which a reflected wave is detected at two points set at a distance of $\lambda/8$ from each other, but there is an advantage in that computation processing is simplified by detecting a reflected wave at two points set at a distance of $\lambda/8$ from each other.

Figure 11:
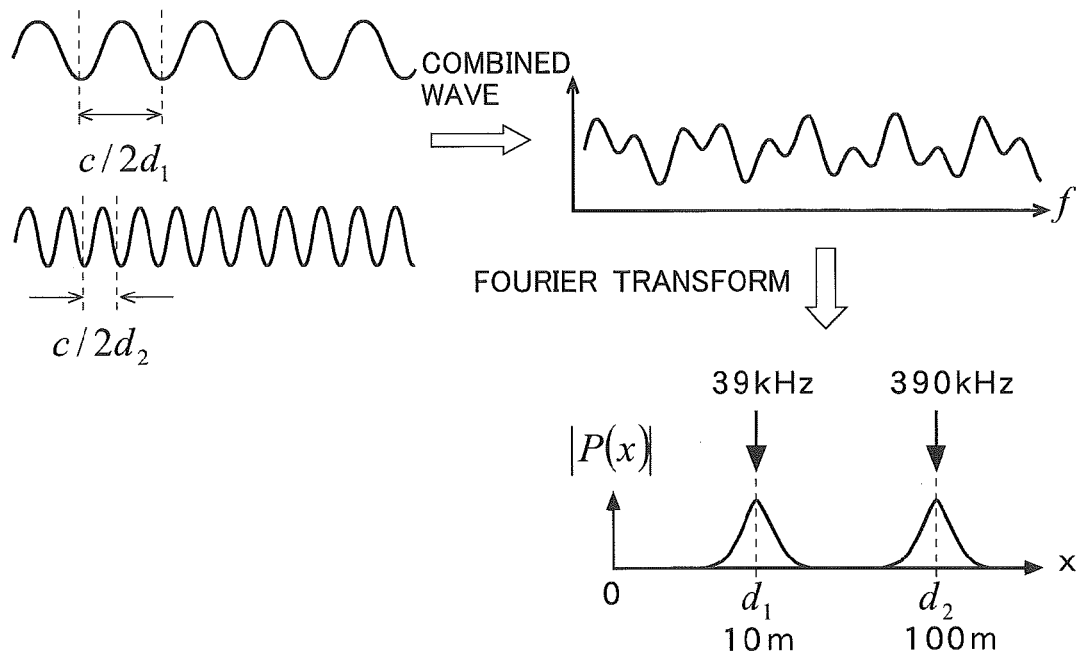
FIG. 11 represents a distance spectrum in the case of two targets.

The distance spectrum when there are two targets is obtained by removing the DC portion from a combined wave of the power p ($f_d$, 0) at $x_s=0$ and the power p($f_d$, $-\lambda/8$) at $x_s=-\lambda/8$ and performing a Fourier transform, thereby obtaining a frequency corresponding to the distance and obtaining the distances $d_1$ and $d_2$, as shown in FIG. 11.

FIG. 12 represents the anti-logarithm spectrum and the imaginary-number spectrum of a combined wave. The speed of radio waves c is about 300,000 km per second. When a frequency sweep of an emitted wave is carried out with a width of 75 MHz (fw), the wavelength at 75 MHz is c/fw=4 m. However, in a sweep for sampling the waveform, the round trip is 4 m, so the outgoing distance is therefore half at 2 m. This 2 m unit is referred to as a single period. In view of the above, 10 periods are measured when 20 m are measured in a sweep width of 75 MHz. When the sweep time is 256 the frequency of the observed waveform is 10/256 μs=39 kHz. Similarly, when 200 m are measured, there are 100 periods, and therefore 100/256 μs=390 kHz. The level of the frequency in the detected spectrum shown in FIG. 12 shows the strength of the reflection, and the frequency can be substituted for distance. Accordingly, as shown in FIG. 11, when a peak is manifest at 39 kHz by Fourier transform, it is apparent that wave is a reflected wave from a position at a distance $d_1=10$ m, and when a peak is manifest at 390 kHz, it is apparent that wave is a reflected wave from a position at a distance $d_2=100$ m. In this manner, when the detection power pa ($f_d$) of the combined wave in the detector is integrated, the DC component is removed, and a Fourier transform is performed, the distance to a reflection object can be obtained.

When the sweep width is 200 MHz, a single period is 0.75 m. Therefore, when the measurement is 10 m, 10/0.75=13.3 periods are observed, and when the sweep time is 256 μs, 13.3/256=51.9 kHz. In other words, when the sweep width is 200 MHz and a peak is manifest at 51.9 kHz, the distance to the reflection object is observed to be 10 m. Therefore, the sweep width and the sweep time are adjusted, whereby the frequency of the detection wave output can be adjusted. Since the bandwidth is limited by restrictions in the Radio Wave law, the distance to the reflection object is generally measured by varying the sweep time.

Next, measurement of very small displacements will be described. In relation to the phase, in Formula 8, the phase related to a kth target is obtained by Formula 14 below, where dk is the amount of change in the distance dk, and $\Delta\phi k$ is the amount of change in phase, resulting in Formula 15 below.

$$b = \sum_{k=1}^{n}\gamma_k\sin\left(\frac{4\pi(f_0+f_d)}{c}d_k - \phi_k\right) \rightarrow \psi_{Ak} = \frac{4\pi f_A}{c}d_k$$ [Formula 14]

$$d_k = \frac{c}{4\pi f_0}\Delta\psi_k$$ [Formula 15]

A very small displacement in the distance d is obtained from Formula 15. When the frequency is 24 GHz, it is possible to sense a displacement of ±3.125 mm.

As described above, the distance and very small displacements of a reflection object can be measured in the signal processor 42 by analyzing a standing wave obtained by combining a reflected wave from the reflection object with the transmitted wave. Chronologically ascertaining the measurement results makes it possible to measure the distance, speed, and displacement of the reflection object, and as a result, the movement of the reflection object. In conventional radar, it is difficult to measure a distance of 1 to 2 m or less, but the present invention makes it possible to measure the distances from nearly 0 m to as far as 200 m. In the case of the present invention, sensing very small displacements is possible, and the relative displacement resolution is as high as 0.01 mm. Furthermore, in the case of a standing-wave radar, abnormalities of the human body can be sensed with high precision because waves pass through clothing and are directly reflected by a clothed human body.

Figure 14:
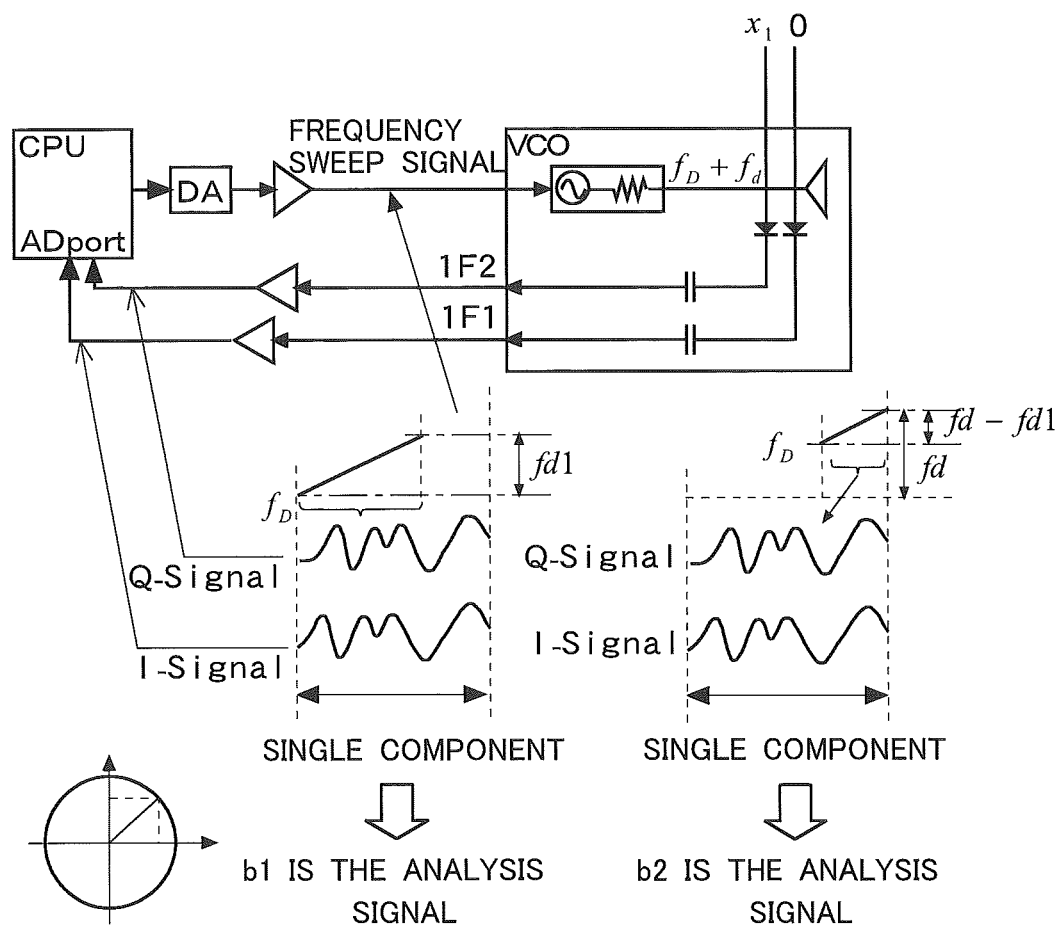
FIG. 14 is a block diagram and waveform diagram showing another embodiment of the present invention.
Figure 15:
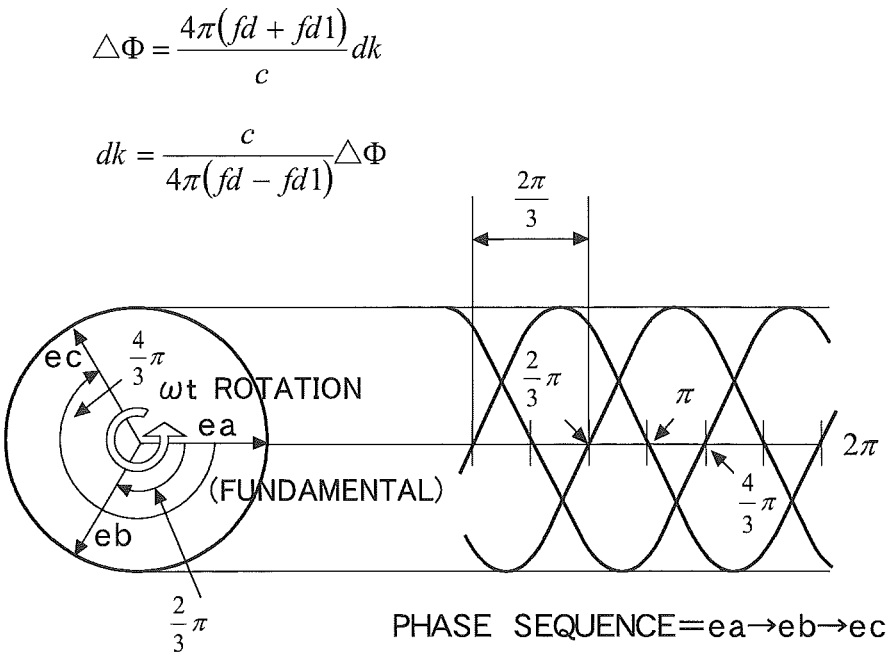
FIG. 15 represents a principle of measuring distance.
Figure 16:
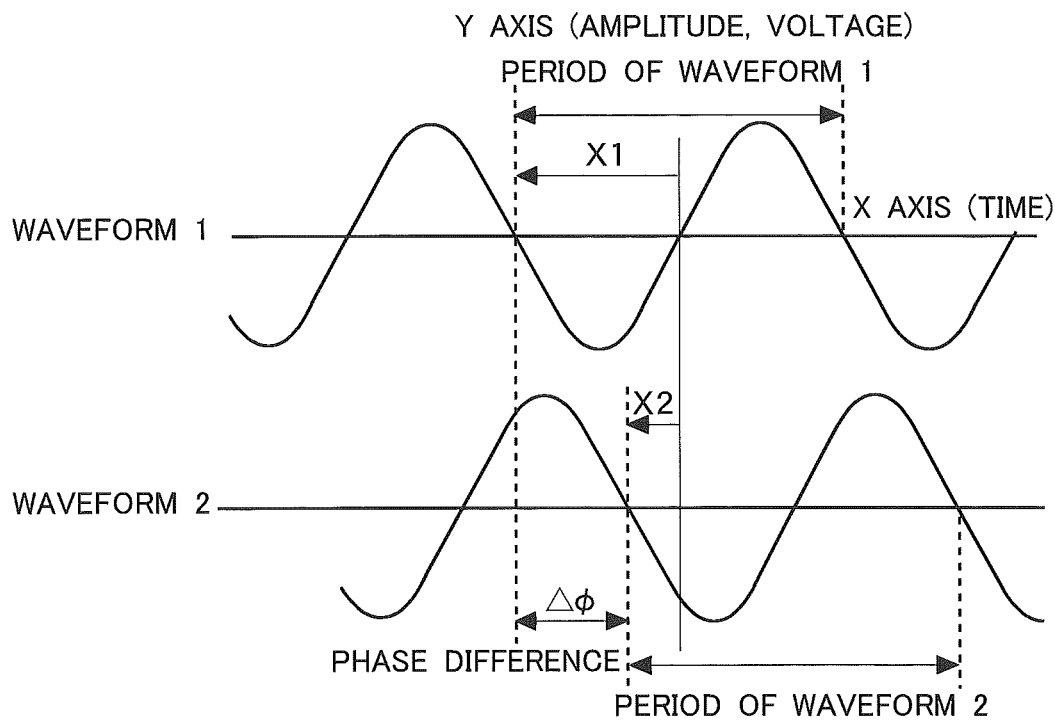
FIG. 16 similarly represents a principle of measuring distance.

Next, another embodiment of the present invention will be described with reference to FIG. 14. The present embodiment senses respiratory rate, heart rate, and other biological information on the basis of Formula 15 above from an analysis signal containing biological information, and the distance to a person to be measured is also sensed. FIG. 14 is a diagram showing the frequency sweep signal (detected wave signal on the real axis and imaginary axis) of the present embodiment. When the center frequency f0 of the emitted wave is, e.g., 24 GHz and the sweep frequency is 75 MHz (fw), analysis is performed in the interval of a single period (75 MHz) with the standing wave being divided into a first-half interval and a second-half interval. In other words, analysis is carried out by Fourier transform and the phases $\Phi 1$ and $\Phi 2$ in the vector plane of the analysis signal of b1 and b2 are represented by Formula 16 and 17 below in similar fashion to Formula 14 above, where b1 is the analysis signal obtained when the oscillator VCO has been varied from a frequency $f_0$ to $f_0+f_{d1}$ (the first-half interval of a single period), and b2 is the analysis signal obtained when the VCO has been varied from a frequency $f_0+f_{d1}$ to $f_0+f_d$ (the second-half interval of a single period). Accordingly, the phase difference $\Delta\Phi$ is obtained by subtracting Formula 16 from Formula 17, giving Formula 18 below. This is shown in FIG. 15, where $2\pi/3$ is the phase difference. This phase difference $\Delta\Phi$ is in a range of 0 to $2\pi$. This phase difference is the phase difference $\Delta\Phi$ of the analysis signal and is not the change in phase ($\Delta\Phi k$ of Formula 15), as shown in FIG. 16.

$$\Phi 1 = \frac{4\pi(f0 + f_d1)}{c}dk - \theta k \qquad [\text{Formula 16}]$$

$$\Phi 2 = \frac{4\pi(f0 + f_d)}{c}dk - \theta k \qquad [\text{Formula 17}]$$

$$\Delta\Phi = \Phi 2 - \Phi 1 = \frac{4\pi(f_d - f_d1)}{c}dk \qquad [\text{Formula 18}]$$

When dk is isolated in Formula 18, Formula 19 below is obtained.

$$dk = \frac{c}{4\pi(f_d - f_d1)}\Delta\Phi \qquad [\text{Formula 19}]$$

By Formula 18, since the speed of light $c=3\times10^8$ (m/sec), the distance dk is calculated to be dk=$3\times108\times(2\pi/3)/4\pi(150\times106-100\times106)$=1.0 m for the case in which the phase difference $\Delta\Phi$ is $2\pi/3$ (120°), where fd=150 MHz and fd1=100 MHz. The measurement range is 0 to $2\pi$, and it is therefore possible to measure distance of 1.0 m to a tripled value at 3 m. In this manner, the physiological state such as the respiratory rate and pulse obtained by very small displacements, as well as the distance d can be obtained from the phase difference.

Figure 17:
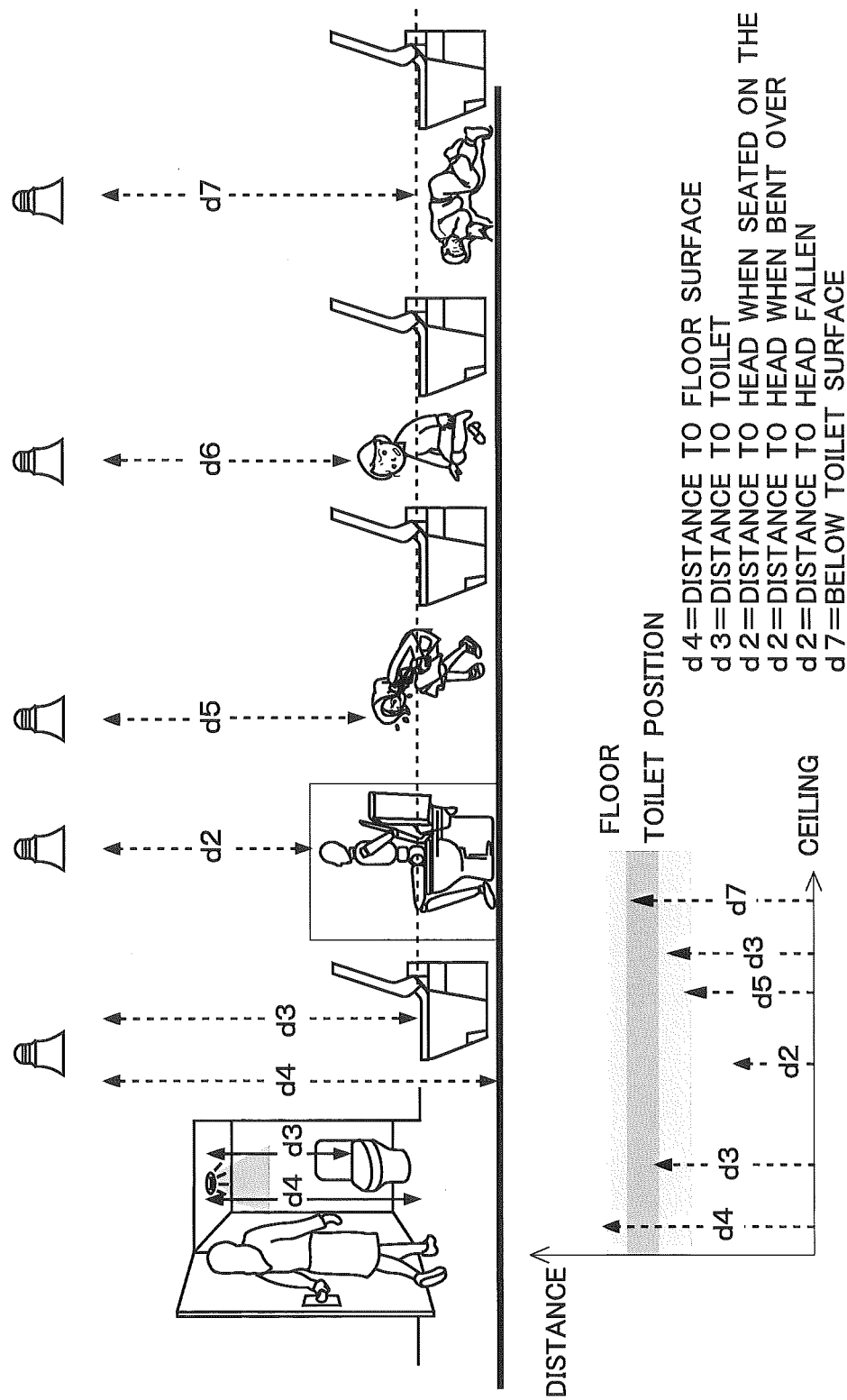
FIG. 17 represents the usage method when the LED illumination apparatus of an embodiment of the present invention has been installed in a restroom.
Figure 19:
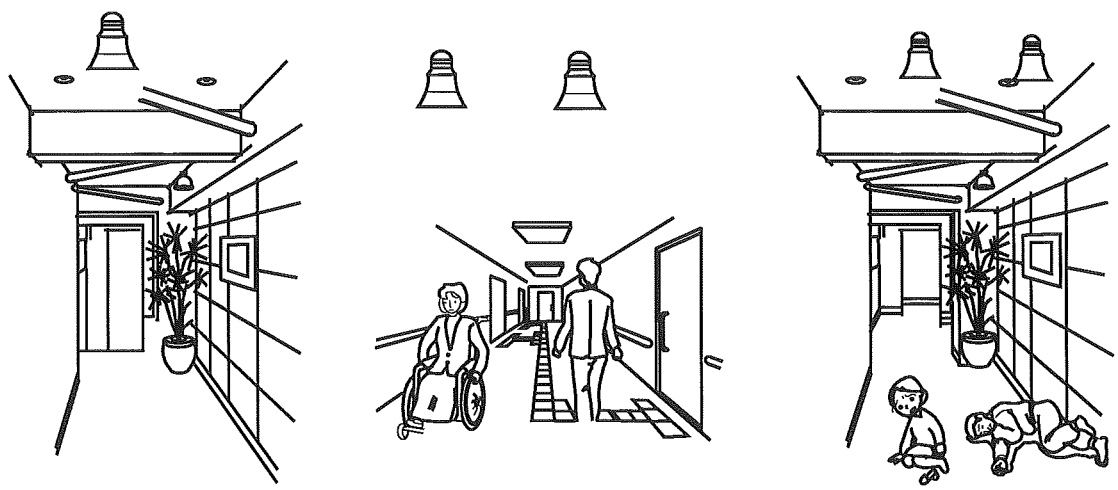
FIG. 19 represents the usage method when the LED illumination apparatus of an embodiment of the present invention has been installed in a hallway.

Next, usage examples of the standing-wave radar-integrated LED illumination apparatus according to embodiments of the present invention installed will be described. FIG. 17 is the case in which the LED illumination apparatus of the present embodiment is installed in the ceiling of a restroom to monitor human body abnormalities. FIG. 18 is the case in which the LED illumination apparatus of the present embodiment is installed in the ceiling of a bathing room to monitor human body abnormalities. FIG. 19 is the case in which the LED illumination apparatus of the present embodiment is installed in the ceiling of a hallway to monitor human body abnormalities.

First, the case in which a resident has fallen in a restroom will be described, as shown in FIG. 17. First, the LED illumination apparatus is installed and a standing wave without the presence of a person is analyzed to thereby measure the distance d4 to the floor surface and the distance d3 to the toilet from the LED illumination apparatus. A resident then enters the restroom, and the distance d2 is measured by the LED illumination apparatus of the present embodiment. The distance d2 is the distance to the head of the resident. At this time, the LED illumination apparatus may be turned on. In this manner, the distance d2, which is different from d3 and d4, is measured, and it is thereby determined that a resident is using the restroom. After a length of time suitable for usage of the restroom has elapsed and when the distance d2 is no longer measured, it is determined that the restroom has been used in an ordinary manner. When observation of the distance d2 has ended, the LED illumination apparatus may be turned off.

On the other hand, when a user is curled up in the restroom and when seated on the floor, an abnormality has occurred in the human body, the distance d5 and the distance d6 are different than the distances d3 and d4 and are greater than the distance d2 to the head when seated on the toilet. It is therefore apparent that an abnormal state has arisen. In this case, if the user is conscious, the LED illumination apparatus detects the movement of the user, it is determined that the object is a human body rather than an article, and the occurrence of an abnormality in the human body can be reliably ascertained. The alarm unit 43 thereby outputs an alarm signal to provide external notification about the abnormal situation of a restroom user. At the same time, it is also possible to display the dangerous state by causing the LED illumination apparatus to blink on and off, causing the amount of light to vary using light modulation, or varying the color temperature (hue). When a portion of the restroom door is translucent glass, a danger display using the above-described LED illumination apparatus is provided as notification to a family member or the like outside the restroom.

When a user has collapsed on the restroom floor and is not conscious, the LED illumination apparatus measures a distance d7 that is different from the distance d2 to the head, and movement of the human body cannot be measured. However, in the present invention, very small displacements can be detected by phase analysis, and the respiratory rate, pulse, and other very small displacements in the human body of the collapsed person can also be detected. In view of the above, the present invention is capable determining that an object is not an article, but is rather a human body that has collapsed. In this case, the standing-wave radar can pass through clothing and directly measure movement on the surface of the human body, and it is therefore possible to more reliably sense an abnormality of the human body. An organism is a reflection object having a reflection coefficient of 0.7 or higher, and it is therefore possible to measure displacement using the surface of the human body and to directly measure skin movement of the human body through clothing. The displacement amplitude of the breathing of an ordinary adult is generally about 2 to 3 mm, and the very small displacement of a standing wave can be measured to about ±3 mm. Therefore, abnormality of a human body can be reliably sensed. Also, when the respiratory rate, pulse, or other danger area or rhythmic pattern is set in advance in the computation unit 31, it is possible to not only differentiate between a human body and an article by detecting respiration or the like, but it is also possible to determine whether or not the respiratory state of the human body is serious.

Figure 20A:
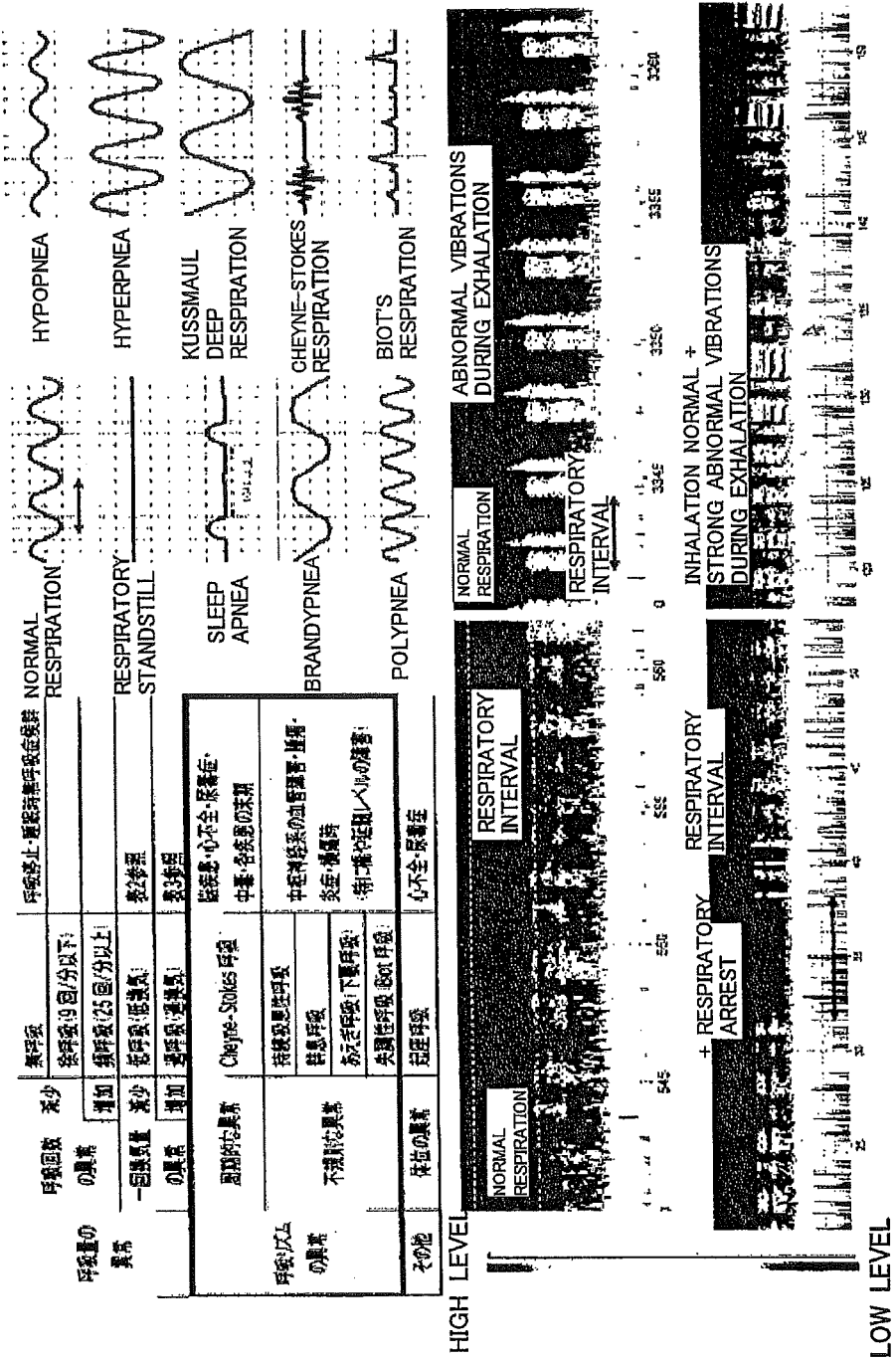

In the case of the bathing room shown in FIG. 18, in the case of a hallway shown in FIG. 19, or in other cases, measurement results are similarly obtained for when a person is not present, and the abnormality of a resident can be determined by excluding the measured distance from the abnormality sensing. At this time, the distance range to be detected during ordinary human body movement is set, and it can be determined that an abnormality has occurred in a resident when a distance outside of this range has been detected. Furthermore, since the respiration and pulse can be measured from very small displacements, it is possible to determine whether an object is a human body, and, if the object is a human body, to what degree the situation is serious. FIG. 20A and FIG. 20B are charts showing the state of measuring a respiratory rate. It is apparent that abnormal respiration can be detected by the present invention, as shown in FIG. 20A and FIG. 20B.

FIG. 21 shows a method for mounting the LED illumination apparatus of an embodiment of the present invention in the ceiling of a train, and analyzing standing waves to determine the level of congestion on a train. Mounting the LED illumination apparatus of an embodiment of the present invention in the ceiling of a train in this manner makes it possible to detect whether the number of human bodies on a train is high or low and to determine the general number thereof. Therefore, a central operations and management center for trains can readily ascertain whether the train is full, congested in an ordinary fashion, or not congested.

FIG. 22 shows a method for mounting the LED illumination apparatus of an embodiment of the present invention in an urban utility pole to provide LED illumination and to determine the water level when a road has been flooded with water and to determine the extent that people are present in the road undergoing this abnormality. In this manner, mounting the LED illumination apparatus of an embodiment of the present invention in a utility pole makes it possible for a disaster prevention center to manage and determine changes in the water level of the road flooded with water, to determine the number of people that have been dispatched to the road in such a case, and to make other determinations.

Figure 23:
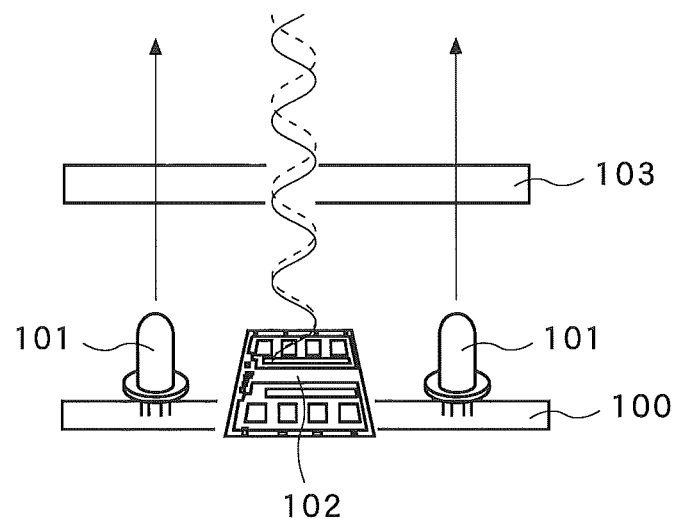
FIG. 23 represents a directly under-type illumination apparatus.

The present invention is not limited to the embodiments described above and can be modified in various ways. For example, FIG. 23 shows another mode of the illumination apparatus of the present invention. The illumination apparatus shown in FIG. 23 is different from the light bulb-type shown in FIG. 2, has LEDs arranged on the obverse side of a sign or other planar light-emitting display surface, and is a directly under-type illumination light. A transceiver 102 for transmitting a radio wave to the exterior and receiving a reflected wave from the exterior is installed in the center position on a board 100. A plurality of LEDs 101 is arranged at, e.g., equidistant intervals about the periphery of the transceiver 102. These LEDs 101 and transceiver 102 are covered by a transparent cover 103. The illumination light from the LEDs 101 is emitted to the exterior via the cover 103, and the transceiver 102 transmits/receives the transmitted wave and the reflected wave via the cover 103. This cover 103 has a light-scattering effect, and LED illumination light scattered from the cover 103 toward the exterior is emitted as smooth illumination light. In this illumination apparatus as well, radio waves can be transmitted from and reflected waves received by the transceiver 102. In this directly under scheme, the LEDs are arranged behind the illumination cover, and LED light is emitted direction to the exterior. Accordingly, the luminous energy of the LED light is high, and the transceiver 102 cannot be disposed behind (below) the metal heat-dissipating board 101, and the installation position of the radar transceiver is restricted. It is apparent that the display surface for planar light emission is not necessarily limited to a sign. A surface such as wall that does not have characters or drawings thereon may also be used in the same manner a sign.

Figure 24:
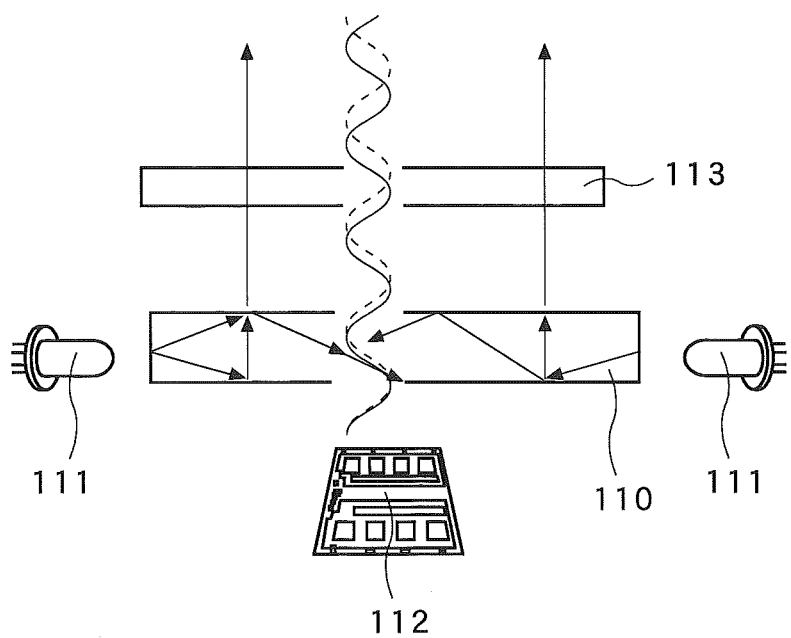
FIG. 24 represents an illumination apparatus in a light guide scheme.

The illumination apparatus shown in FIG. 24 is a light guide scheme illumination apparatus. A radio wave transceiver 112 is arranged behind a light guide plate 110, illumination light emitted from a plurality of LEDs 111 lined up at equidistant intervals is introduced into the light guide plate 110 from the side surface of the light guide plate 110. The illumination light is reflected inside the light guide plate 110 and irradiated from the light guide plate 110 in a direction perpendicular to the surface thereof. A transparent cover 113 is also arranged in front of the light guide plate 110 and the cover 113 also has a light-scattering effect and is capable of irradiating smooth illumination light by scattering. LED light that has entered into the light guide plate 110 is reflected onto the upper and lower surfaces inside the light guide plate 110, the luminous energy forms a substantially uniform plane emission light within the surface, and is emitted to the exterior from the upper surface of the light guide plate 110. In this illumination apparatus as well, a radio wave can be transmitted and a reflected wave can be received from the transceiver 112. In this light guide scheme, the illumination light can be emitted in a planar form, and the position of the radar transceiver 112 may be behind the light guide plate 110 and the installation location is not restricted.

Figure 25:
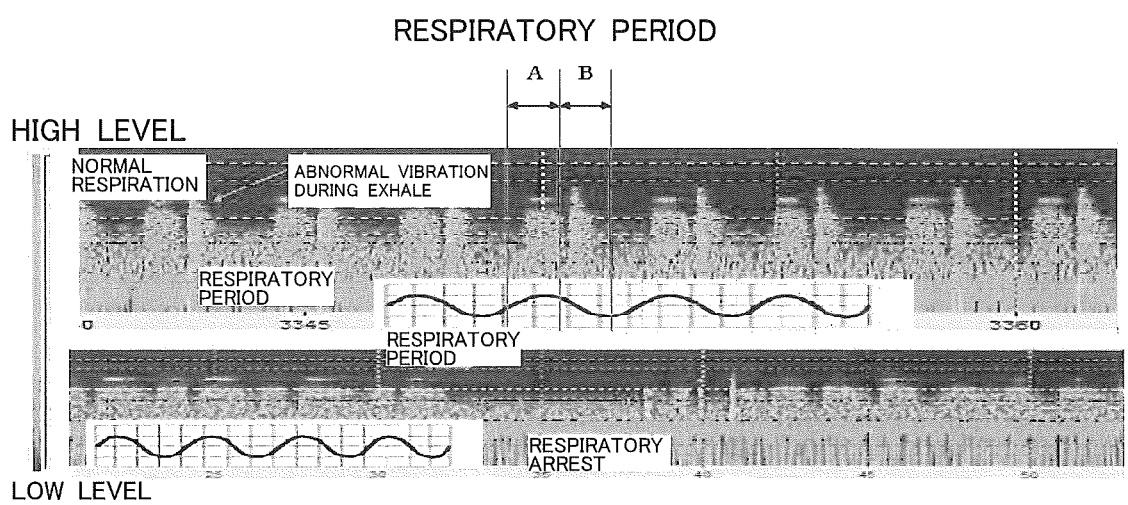
FIG. 25 is a chart obtained by measuring the respiratory period by detecting very small displacement.
Figure 26:
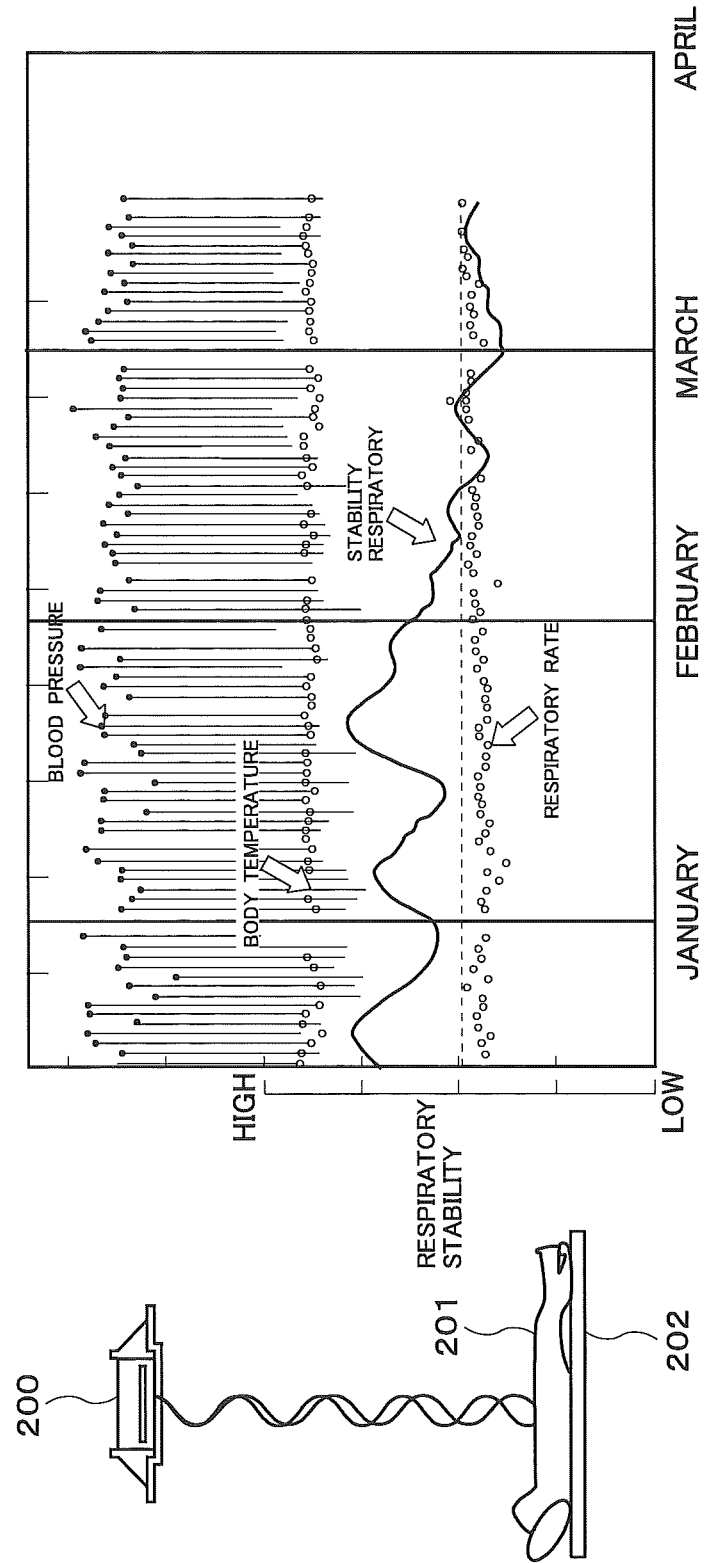
FIG. 26 represents a respiratory rhythm.

FIG. 25 is a chart showing measurements of the respiratory state of a person 201 lying on a bed 202, as shown in FIG. 26, in the form of very small displacements obtained from the amount of phase change in a distance spectrum using the LED-integrated standing-wave radar 200 of the present embodiment disposed in a ceiling. In the case as well of a person lying on a bed, obtaining measurement results of the distance spectrum when a person is not present and eliminating noise produced by the measurement of the bed and other accessory articles makes it possible to determine whether a person is on the bed, and the present invention can be used as a bed-leaving sensor. In this case, the present invention is capable of measuring respiration and pulse from very small displacements, and it is therefore possible to reliably determine whether a measured object is a human body.

On the other hand, the lungs swell when air is inhaled (during inhalation), and the lungs contract with when air is exhaled (during exhalation). In view of this fact, when a time A from a stationary state to a peak value (during inhalation; lungs in swelled state) when air has been inhaled is measured, and a time B from a stationary state to when air is expelled (during exhalation) is measured, then A+B is a respiratory period. In other words, the vertical movement of the lungs of a person 201 is sensed by the standing-wave radar 200 of the present embodiment. In the present embodiment, vertical movement of the chest by respiration of the person 201 can be sensed by the standing-wave radar 200 even when the person 201 is wearing clothing or when the person 201 is covered by bedding. The chart on the right in FIG. 26 shows chronological change in the respiratory rate and respiratory stability of a person 201 on the bed 202 measured by the standing-wave radar 200 of the present embodiment. FIG. 26 also shows the results of separately measured blood pressure and body temperature. In FIG. 26, respiratory stability is related to the magnitude of vertical movement in the respiratory period A+B shown in FIG. 25. In other words, the wave shown in FIG. 25 is larger when the vertical movement of the chest by respiration is great. The magnitude of the vertical movement of the chest increases and decreases, and when the frequency of change in magnitude is high, respiratory stability is considered to be poor. In FIG. 26, the case in which frequency of change in the magnitude of vertical movement of the chest is low is the upper part of the vertical axis of the graph, and respiratory stability is considered to be high; and the case in which frequency of change in the magnitude of vertical movement of the chest is high is the upper part of the vertical axis of the graph. As shown in FIG. 26, the respiratory stability of the person 201 has worsened (trended lower) after two months had elapsed, and it is apparent that respiratory disturbance increased and indications of cardiac failure have appeared. Nevertheless, change in the blood pressure and body temperature are not observed, and no change in the respiratory rate is observed. Accordingly, indications of cardiac failure cannot be sensed by merely monitoring the blood pressure, body temperature, and respiratory rate.

It is well known that heart action is competitively controlled by sympathetic nerves and parasympathetic nerves, and that the heart beat interval constantly fluctuates in periodic fashion. Here, two main frequency components are observed when fluctuation information about the heart beat interval (hereinafter referred to as "heart beat fluctuation information") generated from chronological heart beat interval information is subjected to a frequency analysis. One of the components is a frequency component of 0.05 to 0.15 Hz, which is referred to as a low-frequency (LF) component, and mainly reflects the state of activity of sympathetic nerves and parasympathetic nerves. The other component is a frequency component of 0.15 to 0.45 Hz, which is referred to as a high-frequency (HF) component, and mainly reflects the state of activity of parasympathetic nerves. Since these frequency components reflect autonomous nervous activity, the power of the spectrum thereof is used as an indicator of the state of activity of automatic nerves in tests of automatic nervous function or the like. In a state of rapid eye movement sleep (REM), the voluntary muscles of the body show a state approximate to an awakened brain, even in a relaxed state, and the eyes move often under the eyelids. Non-REM sleep is a state of sound sleep. The first REM sleep appears at about 60 to 120 minutes after the start of sleep, and REM sleep thereafter appears in a repeating fashion between REM sleep and non-REM sleep. The period is generally 90 minutes (90 to 110 minutes), and about three to five periods occur during sleep. In this case, it is known that light sleeping during REM sleep is easier to awaken from than is deep sleep during non-REM sleep. Sleep is considered to be one biological periodic phenomenon (circadian rhythm: a rhythm with a period of about 24 hours) and is controlled by nerve tissue referred to as an internal biological clock.

In the embodiments of the present invention, fluctuation information about heart beat intervals is subjected to a frequency analysis, whereby the time interval, number of cycles, and the like of non-REM sleep and REM sleep can be detected. In view of the above, it is possible to use the device for detecting human body abnormality using standing-wave radar of the present embodiment to sense abnormalities in the sleep state using the heart rate. Also, in accordance with the LED-integrated standing-wave radar of the present embodiment, it is possible to know the timing of non-REM sleep and REM sleep from the heart rate. Therefore, the color temperature of the LEDs can be set to be a red, low color temperature when sleep is being induced prior to going to bed, and the color temperature of the LEDs can be set to be a blue, high color temperature when an awakened state must be induced. The illumination light is thereby modified with suitable timing, whereby an awakened state and a sleep state can be suitably supported, making it possible to contribute to the maintenance of a state of mental health.

INDUSTRIAL APPLICABILITY

In accordance with the present invention, it is possible to sense a person that has collapsed or the like, and the respiratory rate, pulse, and other physiological information of a human body, and it is possible to sense that a human body has fallen into a dangerous state, making a tremendous contribution to securing the safety of a human body.

KEY

1: metal cap
2: case main body
3: cover
5: aluminum board
6: LED
7: standing-wave radar module board
8: standing-wave radar module
10: LED control unit
11: board
12: frame
31: computation unit
35: 24-GHz high-frequency module
42: signal processor

What is claimed is:

1. A device for sensing human body abnormality using standing-wave radar, the device comprising:
   a standing-wave sensor for externally transmitting a frequency-swept radio wave, detecting, at two points separated by a fixed distance, a reflected wave received from an external reflection object based on the transmitted wavelength with X being the wavelength of the transmitted wave, and sensing a standing wave combined from the transmitted wave and the received wave;
   a computation unit for removing a DC component from an intensity distribution of a frequency of the combined wave sensed by said standing-wave sensor, performing a Fourier transform, obtaining a distance spectrum, and computing a change in phase and distance to said reflection object;
   a signal processor for removing a distance component obtained when no person is present in a measurement space from the distance component to the obtained reflection object, and obtaining distance information that is different from the distance component obtained when no person is present in the measurement space to extract the distance component to a person to be measured who has entered into said measurement space; and
   a determination unit for sensing an abnormality in a person to be measured from a variation in the intensity distribution of the component associated with a distance to the person to be measured and determining a physical state of said person to be measured and a physiological state including a respiratory rate and pulse from said change in phase.

2. The device for sensing human body abnormality using standing-wave radar according to claim 1, further comprising:
a case at least partially provided with a transparent cover; and
an LED light source as a light-emitting unit for irradiating illumination light to an exterior via said cover, the LED light source being housed in the case,
said standing-wave sensor, said computation unit, said signal processor, and said determination unit being housed in said case, and said standing-wave sensor transmitting/receiving radio waves via said cover and being housed in an LED illumination apparatus.

3. The device for sensing human body abnormality using standing-wave radar according to claim 2, wherein a power supply unit comprising a connector that is configured to be mounted in a light bulb socket or ceiling is disposed below said case, and power is supplied to said LED light source and said standing-wave sensor via the power supply unit.

4. The device for sensing human body abnormality using standing-wave radar according to claim 2, wherein said computation unit, said signal processor, and said determination unit are housed in said case as a module together with said standing-wave sensor.

5. The device for sensing human body abnormality using standing-wave radar according to claim 2, wherein said determination unit emits an alarm by turning said LED illumination apparatus on and off, or varying the light modulation, when the distance to said person to be measured, or a respiratory rate or a pulse of said person to be measured has been determined to be in a danger area set in advance.

6. The device for sensing human body abnormality using standing-wave radar according to claim 1, wherein said determination unit transmits an alarm signal to an external alarm signal receiver when the distance to said person to be measured, or a respiratory rate or a pulse of said person to be measured has been determined to be in a danger area set in advance.

7. A device for sensing human body abnormality using standing-wave radar, the device comprising:
a standing-wave sensor for externally transmitting a frequency-swept radio wave, detecting, at two points separated by a fixed distance, a reflected wave received from an external reflection object based on the transmitted wavelength with X being the wavelength of the transmitted wave, and sensing a standing wave combined from the transmitted wave and the received wave;
a computation unit for removing a DC component from an intensity distribution of a frequency of the combined wave sensed by said standing-wave sensor, performing a Fourier transform, obtaining a distance spectrum, and computing from the distance spectrum of a first interval and the distance spectrum of a second interval in a single period a phase difference from the distance spectra and a change in phase;
a signal processor for removing a distance component obtained when no person is present in a measurement space from the distance component to the reflection object obtained from said phase difference, and obtaining distance information that is different from the distance component obtained when no person is present in the measurement space to extract the distance component to a person to be measured who has entered into said measurement space; and
a determination unit for sensing an abnormality in a person to be measured from a variation in the intensity distribution of the component associated with a distance to the person to be measured and determining a physical state of said person to be measured and a physiological state including a respiratory rate and pulse from said change in phase.

8. The device for sensing human body abnormality using standing-wave radar according to claim 7, further comprising:
a case at least partially provided with a transparent cover; and
an LED light source as a light-emitting unit for irradiating illumination light to an exterior via said cover, the LED light source being housed in the case, said standing-wave sensor, said computation unit, said signal processor, and said determination unit being housed in said case, and said standing-wave sensor transmitting/receiving radio waves via said cover and being housed in an LED illumination apparatus.

9. The device for sensing human body abnormality using standing-wave radar according to claim 8, wherein a power supply unit comprising a connector that is configured to be mounted in a light bulb socket or ceiling is disposed below said case, and power is supplied to said LED light source and said standing-wave sensor via the power supply unit.

10. The device for sensing human body abnormality using standing-wave radar according to claim 8, wherein said computation unit, said signal processor, and said determination unit are housed in said case as a module together with said standing-wave sensor.

11. The device for sensing human body abnormality using standing-wave radar according to claim 8, wherein said determination unit emits an alarm by turning said LED illumination apparatus on and off, or varying the light modulation, when the distance to said person to be measured, or a respiratory rate or a pulse of said person to be measured has been determined to be in a danger area set in advance.

12. The device for sensing human body abnormality using standing-wave radar according to claim 7, wherein said determination unit transmits an alarm signal to an external alarm signal receiver when the distance to said person to be measured, or a respiratory rate or a pulse of said person to be measured has been determined to be in a danger area set in advance.

13. A method for using a device for sensing human body abnormality using standing-wave radar, comprising:
utilizing the device for sensing human body abnormality using standing-wave radar according to claim 1; and
installing the device in a ceiling of a building or a residence to determine an abnormality of a human body inside the residence or the building.

14. A method for using a device for sensing human body abnormality using standing-wave radar, comprising:
utilizing the device for sensing human body abnormality using standing-wave radar according to claim 1; and
installing the device in a ceiling of a vehicle or a ceiling of a passage or a tunnel to determine congestion of human bodies therein.

15. A method for using a device for sensing human body abnormality using standing-wave radar, comprising:
utilizing the device for sensing human body abnormality implemented by the LED illumination apparatus according to claim 2; and installing the device for illuminating a road using said LED light source, and a water level of water that has flooded the road and congestion of human bodies positioned in the road are determined.

16. A method for using a device for sensing human body abnormality using standing-wave radar, comprising:
   utilizing the device for sensing human body abnormality using standing-wave radar according to claim 7; and
   installing the device in a ceiling of a building or a residence to determine an abnormality of a human body inside the residence or the building.

17. A method for using a device for sensing human body abnormality using standing-wave radar, comprising:
   utilizing the device for sensing human body abnormality using standing-wave radar according to claim 7; and
   installing the device in a ceiling of a vehicle or a ceiling of passage or a tunnel to determine congestion of human bodies therein.

18. A method for using a device for sensing human body abnormality using standing-wave radar, comprising:
   utilizing the device for sensing human body abnormality implemented by the LED illumination apparatus according to claim 8; and
   installing the device for illuminating a road using said LED light source, and a water level of water that has flooded the road and congestion of human bodies positioned in the road are determined.

* * * * *